United States Patent
Cox et al.

(10) Patent No.: US 6,730,016 B1
(45) Date of Patent: May 4, 2004

(54) CARDIAC DISEASE TREATMENT AND DEVICE

(75) Inventors: James Cox, Hamel, MN (US); Michael J. Girard, Lino Lakes, MN (US); Donald F. Palme, II, Princeton, MN (US); Donald G. Rohrbaugh, Minnetonka, MN (US); Hani N. Sabbah, Waterford, MI (US); J. Edward Shapland, II, Vadnais Heights, MN (US); Robert G. Walsh, Lakeville, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 210 days.

(21) Appl. No.: 09/591,875

(22) Filed: Jun. 12, 2000

(51) Int. Cl.[7] .............................. A61F 2/00; A61F 13/00
(52) U.S. Cl. ........................................................ 600/37
(58) Field of Search ............................... 600/37, 18, 17, 600/16; 424/422, 423, 424, 426, 427, 430, 434, 437, 489, 490; 514/814, 866, 822; 523/112, 113; 427/2.24, 2.25; 128/897; 606/151, 154; 607/129

(56) References Cited

U.S. PATENT DOCUMENTS

| | | |
|---|---|---|
| 4,048,990 A | 9/1977 | Goetz |
| 4,428,375 A | 1/1984 | Ellman |

(List continued on next page.)

FOREIGN PATENT DOCUMENTS

| | | |
|---|---|---|
| DE | 295 17 393 U 1 | 3/1996 |
| EP | 0 280 564 A2 | 8/1988 |
| JP | 60-203250 A2 | 10/1985 |
| JP | 01-145066 A | 6/1989 |
| SU | 1009457 A | 4/1983 |
| WO | WO 98/29041 | 7/1998 |
| WO | WO 98/58598 | 12/1998 |
| WO | WO 99/16381 | 4/1999 |
| WO | WO 99/44534 | 9/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |

OTHER PUBLICATIONS

Levin, H. et al., "Reversal of Chronic Venticular Dilation in Patients With End–Stage Cardiomyopathy by Prolonged Mechanical Unloading", *Circulation*, vol. 91, No. 11, pp. 2717–2720 (Jun. 1, 1995).

(List continued on next page.)

*Primary Examiner*—Max F. Hindenburg
*Assistant Examiner*—Brian Szmal
(74) *Attorney, Agent, or Firm*—Merchant & Gould P.C.

(57) ABSTRACT

A device for treating cardiac disease of a heart having an upper portion and a lower portion divided by an A-V groove, the device including a jacket adapted to be secured to the heart, and a non-adherent material in association with the jacket. The jacket is fabricated from a flexible material defining a volume between an upper and a lower end, the jacket being adapted to be adjusted on the heart to snugly conform to an external geometry of the heart and assume a maximum adjusted volume for the jacket to constrain expansion of the heart beyond the maximum adjusted volume during diastole and permit substantially unimpeded contraction of the heart during systole. As a result of the flexible material, the jacket allows unimpeded diastolic filling of the heart. Also described is a method for treating cardiac disease including surgically accessing the heart, applying the treatment device of the invention, securing the treatment device to the heart, and surgically closing access to the heart while leaving the treatment device on the heart.

36 Claims, 9 Drawing Sheets

U.S. PATENT DOCUMENTS

| | | | |
|---|---|---|---|
| 4,506,680 A | | 3/1985 | Stokes |
| 4,630,597 A | | 12/1986 | Kantrowitz et al. |
| 4,690,134 A | | 9/1987 | Snyders |
| 4,821,723 A | | 4/1989 | Baker, Jr. et al. |
| 4,878,890 A | | 11/1989 | Bilweis |
| 4,936,857 A | | 6/1990 | Kulik |
| 4,957,477 A | | 9/1990 | Lundback |
| 4,973,300 A | | 11/1990 | Wright |
| 4,976,730 A | | 12/1990 | Kwan-Gett |
| 5,057,117 A | | 10/1991 | Atweh |
| 5,087,243 A | | 2/1992 | Avitall |
| 5,131,905 A | | 7/1992 | Grooters |
| 5,150,706 A | | 9/1992 | Cox et al. |
| 5,186,711 A | | 2/1993 | Epstein |
| 5,192,314 A | | 3/1993 | Daskalakis |
| 5,256,132 A | | 10/1993 | Snyders |
| 5,290,217 A | | 3/1994 | Campos |
| 5,356,432 A | | 10/1994 | Rutkow et al. |
| 5,383,840 A | | 1/1995 | Heilman et al. |
| 5,385,156 A | | 1/1995 | Oliva |
| 5,429,584 A | | 7/1995 | Chiu |
| 5,507,779 A | | 4/1996 | Altman |
| 5,524,633 A | | 6/1996 | Heaven et al. |
| 5,603,337 A | | 2/1997 | Jarvik |
| 5,647,380 A | | 7/1997 | Campbell et al. |
| 5,702,343 A | | 12/1997 | Alferness |
| 5,711,959 A | * | 1/1998 | Kohler et al. ............... 424/423 |
| 5,713,954 A | | 2/1998 | Rosenberg et al. |
| 5,800,528 A | | 9/1998 | Lederman et al. |
| 5,800,828 A | * | 9/1998 | Dionne et al. ............. 424/422 |
| 5,961,440 A | | 10/1999 | Schweich, Jr. et al. |
| 5,990,378 A | | 11/1999 | Ellis |
| 6,045,497 A | | 4/2000 | Schweich, Jr. et al. |
| 6,050,936 A | | 4/2000 | Schweich, Jr. et al. |
| 6,059,715 A | | 5/2000 | Schweich, Jr. et al. |
| 6,143,354 A | * | 11/2000 | Koulik et al. ............... 427/2.24 |
| 6,155,972 A | * | 12/2000 | Nauertz et al. ............... 600/37 |
| 6,293,906 B1 | * | 9/2001 | Vanden Hoek et al. ....... 600/37 |
| 6,425,856 B1 | * | 7/2002 | Shapland et al. ............. 600/37 |

OTHER PUBLICATIONS

Oh, J. et al., "The Effects Of Prosthetic Cardiac Binding and Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, D., "Warp Knitting Technology", *Columbine Press*, p. 111 (1965).

Vaynblat, M. et al., "Cardiac Binding in Experimental Heart Failure", *Am. Thorac. Surg.*, vol. 64, 11 pages, (1997).

"Supplement to Circulation", *Abstracts from the 68th Scientific Sessions*, vol. 92, No. 8, 2 pages (Oct. 15, 1995).

Capomolla, S. et al., "Dobutamine and nitroprusside infusion in patients with severe congestive heart failure: Hemodynamic improvement by discordant effects on mitral regurgitation, left atrial function, and ventricular function", *American Heart Journal*, pp. 1089–1098 (Dec. 1997).

Capouya, E. et al., "Girdling Effect of Nonstimulated Cardiomyoplasty on Left Ventricular Function", *Ann. Thorac. Surg.*, vol. 56, pp. 867–871 (1993).

Cohn, J., "The Management of Chronic Heart Failure", *The New England Journal of Medicine*, vol. 335, No. 7, pp. 490–498 (Aug. 15, 1996).

Coletta, C. et al., Prognostic value of left ventricular volume response during dobutamine stress echocardiography:, *European Heart Journal*, vol. 18, pp. 1599–1605 (Oct. 1997).

Guasp, F., "Una prótesis contentiva para el tratamiento de la miocardiopatia dilatada", *Revista Española de Cardiologia*, vol. 51, No. 7, pp. 521–528 (Jul. 1998).

Kass, D. et al., "Reverse Remodeling From Cardiomyoplasty in Human Heart Failure External Constraint Versus Active Assist", *Circulation*, vol. 91, No. 9, pp. 2314–2318 (May 1, 1995).

* cited by examiner

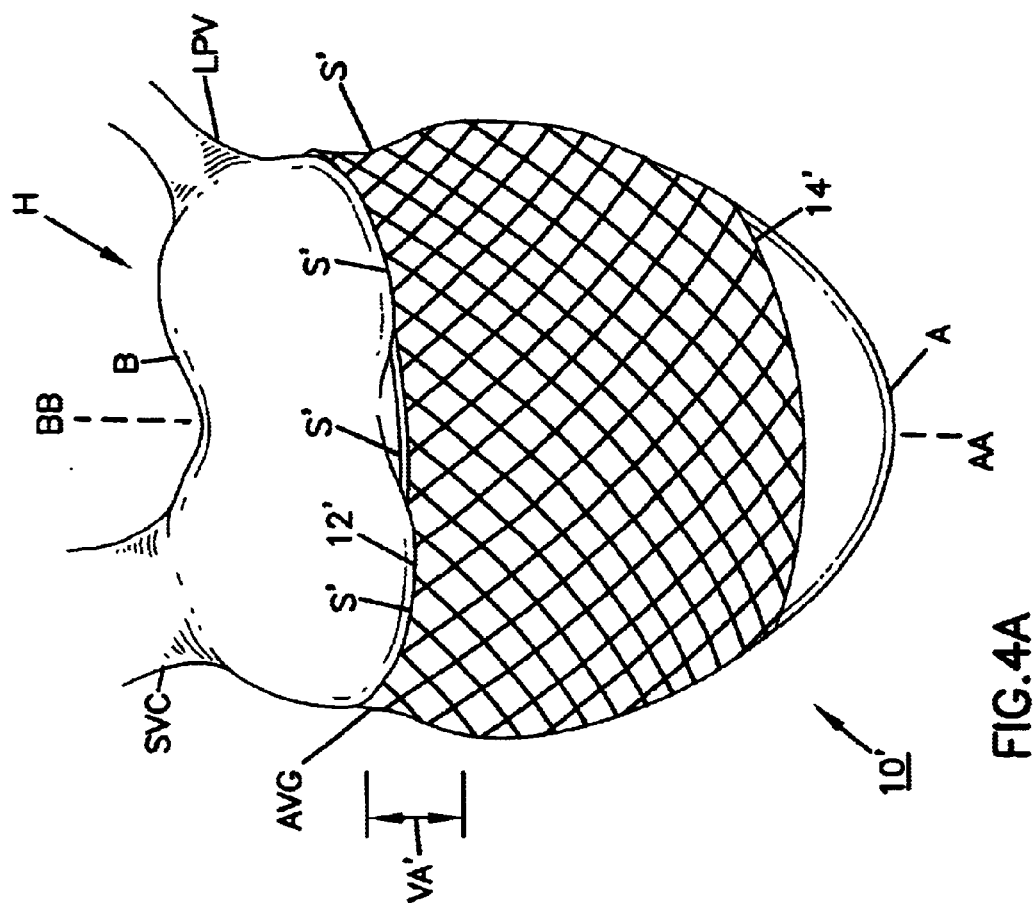
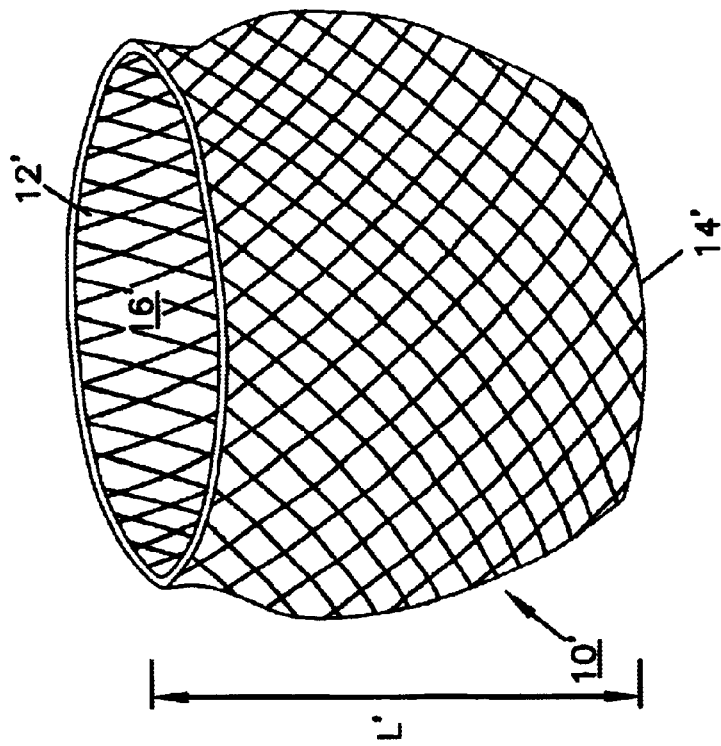
FIG. 4A
FIG. 4

CARDIAC DISEASE TREATMENT AND DEVICE

FIELD OF THE INVENTION

The present invention relates a device and method for treatment of cardiac disease and related cardiac complications. In particular, the present invention relates to a device for treating cardiac disease that includes a jacket that is adapted to be secured to the heart, and non-adherent material provided in association with the jacket.

BACKGROUND OF THE INVENTION

Chronic or congestive heart disease is a progressive and debilitating illness. The disease is characterized by a progressive enlargement of the heart. Often, heart failure develops as a consequence of coronary artherosclerosis and myocardial infarction. After an infarction, the irreversibly injured myocardium is gradually replaced with fibrous scar tissue, since myocytes have limited ability to proliferate, and lost myocytes cannot regenerate. As myocytes are replaced with fibroblasts and collagen, changes in the mechanics of the heart lead to progressive onset of congestive heart failure.

As the heart enlarges, the heart is performing an increasing amount of work in order to pump blood with each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., NYHA Classes I, II, III and IV). In the early stages (e.g., Classes I and II), drug therapy is the commonly proscribed treatment. Drug therapy treats the symptoms of the disease and may slow the progression of the disease. Importantly, there is no cure for congestive heart disease. Even with drug therapy, the disease will progress. Further, the drugs may have adverse side effects, particularly when they are administered through the bloodstream.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1–2 years for a donor heart. While the availability of donor hearts has historically increased, the rate of increase is slowing dramatically. Even if the risks and expense of heart transplant could be tolerated, this treatment option is becoming increasingly unavailable. Further, many patient's do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease and related complications. One alternative treatment is described in commonly assigned U.S. Pat. No. 5,702,343 to Alferness dated Dec. 30, 1997 teaches a jacket to constrain cardiac expansion during diastole. The present invention pertains to improvements to the invention disclosed in the '343 patent.

SUMMARY OF THE INVENTION

The present invention provides a device and method for treating cardiac disease and related cardiac complications. According to the invention, the device comprises a jacket that is adapted to be secured to the heart, and a non-adherent material in association with the jacket. Preferably, the non-adherent material prevents unwanted fibrosis or adhesion to the heart as a result of the presence of the jacket on the heart surface. The non-adherent material can be formed as an integral part of the jacket, or can be provided as a separate element of the overall device. Positioning of the non-adherent material can be controlled to reduce the risk of fibrosis or other adverse effects on the surface of the heart or surrounding organs. Preferably, the non-adherent material is located within or on the jacket such that it overlies areas of the heart surface containing major blood vessels, to facilitate access to those blood vessels, if the need should arise. The non-adherent material also facilitates removal of the jacket, if such removal becomes desirable or necessary. In one embodiment, the non-adherent material comprises a coating on the jacket. Alternatively, the non-adherent material comprises a separable element of the device and is provided in connection with the jacket.

In one embodiment, a device for treating cardiac disease comprises a jacket of flexible material that is secured to the heart and conforms to an external geometry of the heart, and a non-adherent material to prevent unwanted fibrosis on the surface of the heart. Preferably, the jacket is adapted to be adjusted on the heart to snugly conform to an external geometry of the heart and assume a maximum adjusted volume for the jacket to constrain expansion of the heart beyond the maximum adjusted volume during diastole and permit substantially unimpeded contraction of the heart during systole. In one aspect, the non-adherent material is adapted to cover only a specific area, or the entire surface area, of the heart.

In another embodiment, methods for treating cardiac disease and related cardiac complications are described, the method comprising surgically accessing the heart; applying a treatment device on the heart, the device comprising a jacket of flexible material that is secured to the heart and conforms to an external geometry of the heart, and a non-adherent material in association with the jacket; securing the treatment device to the heart; and surgically closing access to the heart while leaving the treatment device on the heart.

BRIEF DESCRIPTION OF THE DRAWINGS

FIG. 4 is a perspective view of a second embodiment of a cardiac constraint device according to the present invention;

FIG. 4A is a side elevation view of a diseased heart in diastole with the device of FIG. 4 in place;

DETAILED DESCRIPTION

Figure 1:
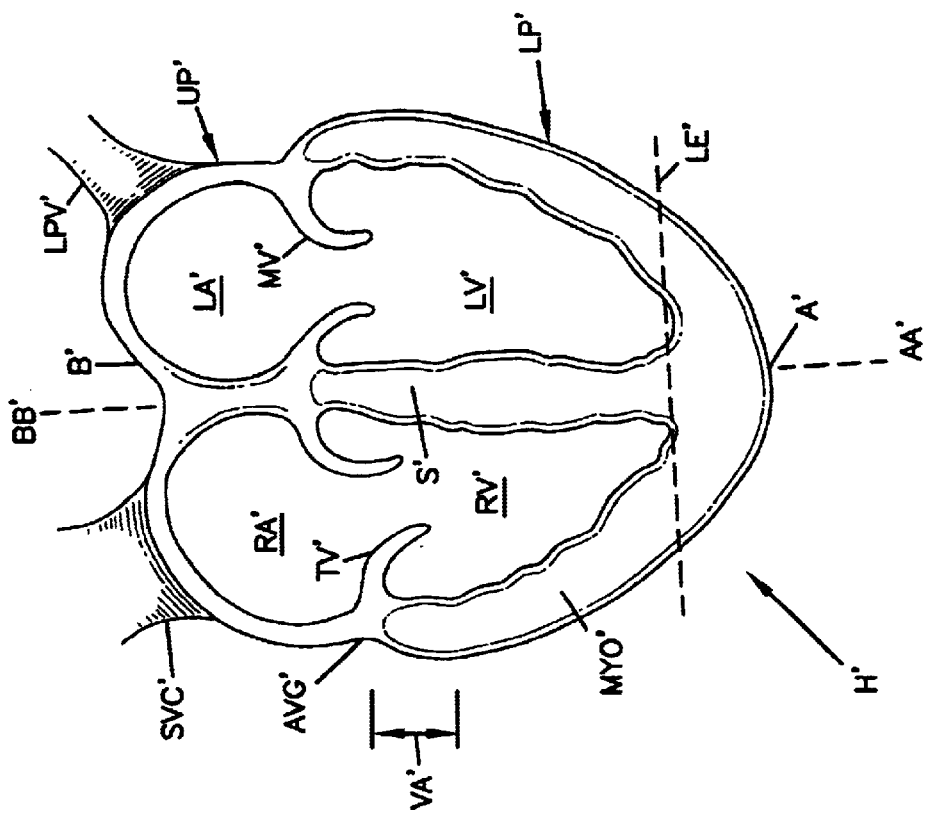
FIG. 1 is a schematic cross-sectional view of a normal, healthy human heart shown during systole.

The present invention provides devices and methods for treatment of cardiac conditions such as cardiomyopathy, valvular insufficiency, arrhythmias, and other cardiac complications. Generally, the invention is directed to a jacket that is secured to the heart and constrains expansion of the heart during diastole to a predetermined limit, and a delivery source for the delivery of a therapeutic agent to the surface of the heart.

The present invention provides advantages over known methods of treatment for cardiac disorders. Many known methods of drug treatment involve delivering the drugs to the site of action through the bloodstream. The amount of time required for these drugs to have the desired effect, and how long their effects last often depend upon several factors, including how quickly the drugs get into the bloodstream, how much of them gets into the bloodstream, how quickly they leave the bloodstream, how efficiently they are broken down (metabolized) by the liver, and how quickly they are eliminated by the kidneys and intestines. A drug may move slowly from the bloodstream into the body's tissues. Moreover, drugs penetrate different tissues at different speeds, depending upon their ability to cross membranes. In general, fat-soluble drugs can cross cell membranes more quickly than water-soluble drugs.

Intravenous administration of a drug may present adverse side effects when the systemic level of a drug exceeds a tolerable limit. Distribution of a drug may be further complicated when the drug is administered into the bloodstream. Once absorbed, most drugs do not spread out evenly through the body. Some drugs tend to stay within the watery tissues of the blood and muscles, while others concentrate in specific tissues such as the thyroid gland, liver, and kidneys. Additionally, some drugs bind tightly to blood proteins, leaving the bloodstream very slowly, while others escape from the bloodstream quickly into other tissues. Some tissues build up such high levels of a drug that they serve as reservoirs of extra drug, thereby prolonging the drug's distribution. In fact, some drugs, such as those that accumulate in fatty tissues, leave these tissues slowly and consequently circulate in the bloodstream for some days after a person has stopped taking the drug.

In contrast, localized, targeted delivery of the drug can avoid undesirable systemic effects by eliminating circulation of the drug in areas of the body other than the target tissue. It would be beneficial to be able to treat congestive heart disease or other related cardiac disorder with a drug while avoiding undesirable systemic effects such as drug-associated systemic toxic effects.

The present invention provides a combination of such advantages as controllability of therapeutic agent delivery (including duration of exposure to the agent, dosage, and size of the target area to be exposed to the agent), and contact between the therapeutic agent and the target surface that is intimate, long-term, and non-shifting. The present invention can target delivery of the therapeutic agent to a specific target area on or around the heart. If desired, the entire surface of the heart can be treated with the agent, or one or more specific areas of the heart can be treated. The ability to target the therapeutic agent as desired avoids adverse systemic effects of therapeutic agents.

The present invention maintains a controlled release of the therapeutic agent after implantation of the device. According to the present invention, the delivery source for delivery of a therapeutic agent to the surface of the heart is provided in non-shifting contact with the heart surface, allowing sustained treatment of a defined area of the heart. The present invention also provides a flexible device for delivery of the therapeutic agent, such that the device maintains intimate contact with the heart during delivery of the agent. This intimate, non-shifting contact with the heart achieves local delivery of a therapeutic agent that might otherwise be impossible or at least difficult to deliver as a result of such factors as poor blood flow to the target surface, for example, as a result of ischemia. Because the present invention delivers the therapeutic agent directly to a localized target surface, lower amounts, but potentially higher localized concentrations, of the therapeutic agent can be delivered.

The invention is not limited to treatment of the heart. The device and method can be used to treat tissues surrounding the heart or other tissues of the body, as desired. The invention thus provides controlled release of a therapeutic agent to tissues of the body.

In one preferred embodiment, the mechanical energy of the heart drives drug delivery. In this embodiment, for example, the pressure of the heart against the jacket of the device controls release of the therapeutic agent from the delivery source of the device. In another preferred embodiment, the present invention can expose the target tissue to a combination of agents, when treatment with more than one type of agent is desired. For example, one or more anti-arrhythmic drugs and one or more desired antibiotics can be provided in connection with the device, when the physician determines that both the rhythm of the heart and potential infections are to be controlled.

Figure 1A:
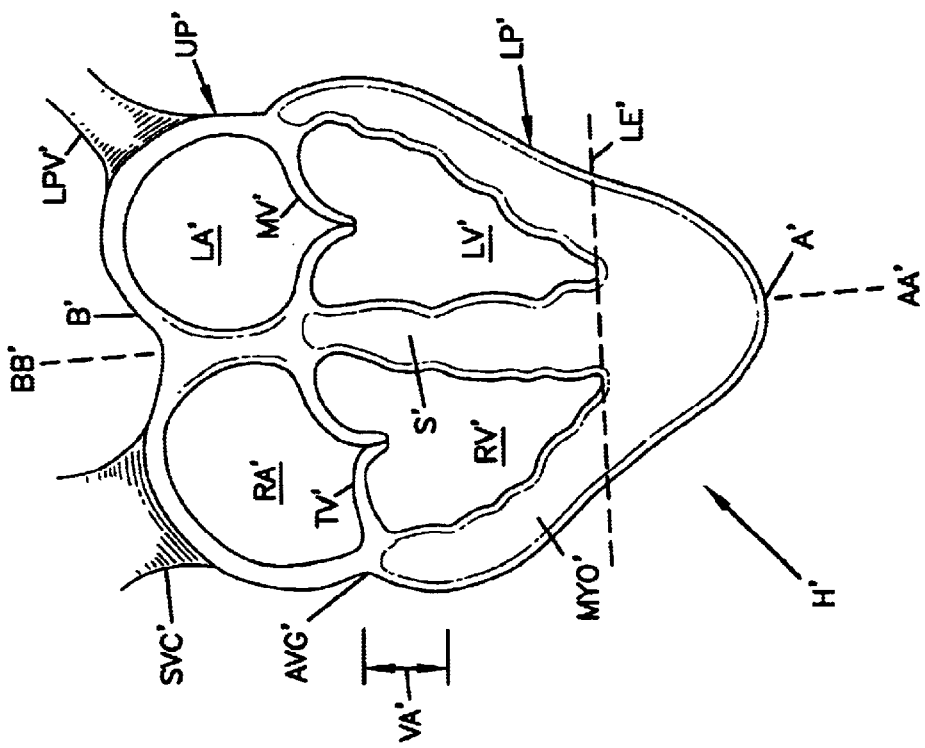
FIG. 1A is the view of FIG. 1 showing the heart during diastole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis AA'-BB' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H'. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2B:
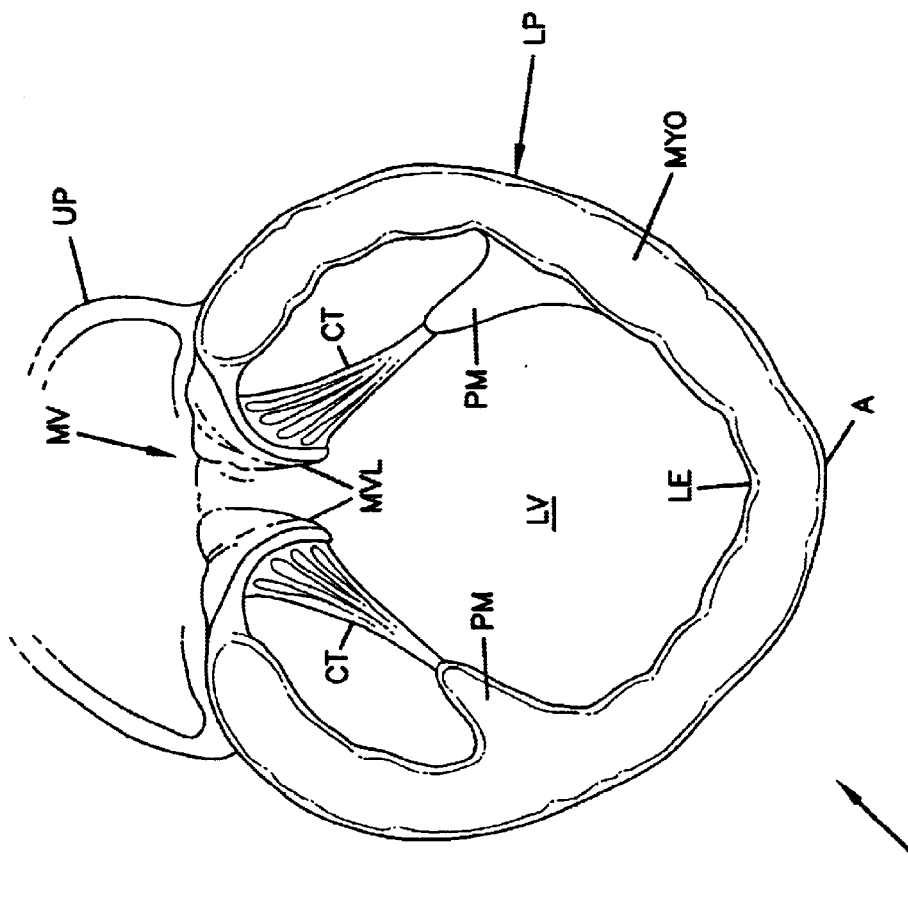
FIG. 2B is the view of FIG. 1B showing a diseased heart.
Figure 2A:
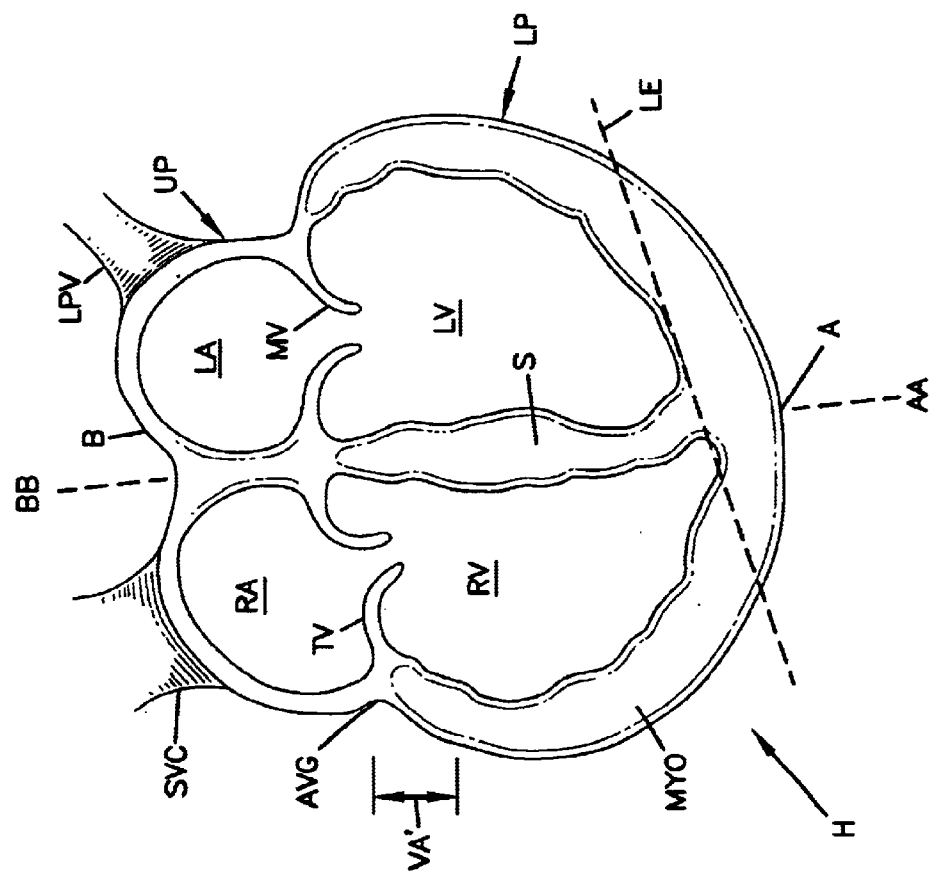
FIG. 2A is the view of FIG. 2 showing the heart during diastole.
Figure 2:
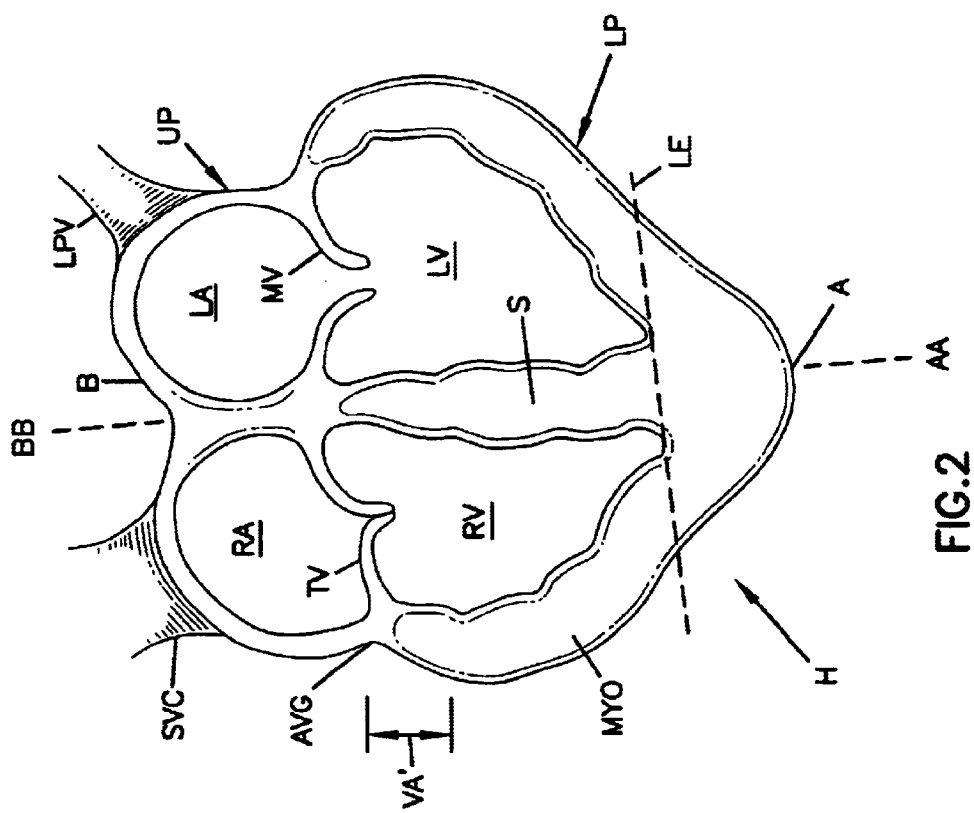
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy, with greater oxygen demand, to pump the same amount of blood. Continued progression of the disease results in the heart H being unable to supply adequate blood to the patient's body and the patient exhibits symptomatic insufficiency.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 1B:
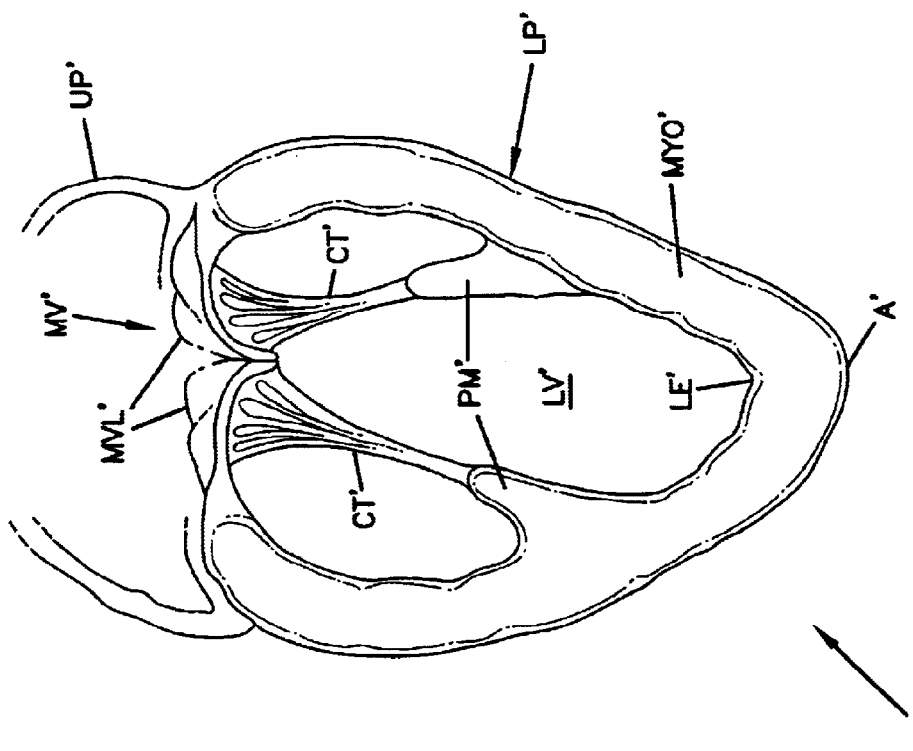
FIG. 1B is a view of a left ventricle of a healthy heart as viewed from a septum and showing a mitral valve.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

Having described the characteristics and problems of congestive heart disease, the treatment method and apparatus of the present invention will now be described.

The device of the present invention comprises a jacket adapted to be secured to the heart and a delivery source for delivery of one or more therapeutic agents to the heart. In general, a jacket of the invention is configured to surround the myocardium MYO. As used herein, "surround" means that the jacket provides reduced expansion of the heart wall at end diastole by applying constraining surfaces at least at diametrically opposing aspects of the heart. In some preferred embodiments disclosed herein, the diametrically opposed surfaces are interconnected, for example, by a continuous material that can substantially encircle the external surface of the heart. The jacket is also preferably fabricated from a flexible material to allow unrestricted filling of the heart during diastole.

With reference now to FIGS. 3, 3A, 4 and 4A, the device of the present invention is shown as a jacket 10 of flexible, biologically compatible material. As used herein, "biologically compatible material" means material that is not biologically adverse such that the material will not cause adverse effects to surrounding tissues, such as rejection, infection, inflammation, and the like. Such material can be a biostable material such as a biostable polymer, or a biodegradable material, as discussed in more detail below.

The jacket 10 is an enclosed knit material having upper and lower ends 12, 14. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Alternatively, upper ends 12, 12' can be closed while allowing the SVC, LVC and other blood vessels to pass through the jacket material. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to the valvular annulus VA and further extends to the lower portion LP to constrain at least the lower ventricular extremities LE.

The jacket of the invention can be provided in any suitable size and shape for application to the heart. In one embodiment, for example, the jacket 10 is provided in a conical shape. As used herein, "conical" refers to a shape of the jacket wherein the diameter of the jacket decreases from the upper end 12, 12' towards the lower end 14, 14', to approximate the ellipsoid shape of the heart. In one embodiment, the size of the jacket 10 is predetermined, such that the jacket is fabricated in a conical shape prior to application to the heart. Alternatively, the shape of the jacket is adjusted at the time of placement of the device on the heart.

Since enlargement of the lower portion LP is most troublesome, in a preferred embodiment, the jacket 10 is sized so that the upper end 12 can reside in the A-V groove AVG. Where it is desired to constrain enlargement of the upper portion UP, the jacket 10 may be extended to cover the upper portion UP.

Sizing the jacket 10 for the upper end 12 to terminate at the A-V groove AVG may be desirable for a number of reasons. First, the groove AVG is a readily identifiable anatomical feature to assist a surgeon in placing the jacket 10. By placing the upper end 12 in the A-V groove AVG, the surgeon is assured the jacket 10 will provide sufficient constraint at the valvular annulus VA. The A-V groove AVG and the major vessels act as natural stops for placement of the jacket 10 while assuring coverage of the valvular annulus VA. Using such features as natural stops is particularly beneficial in minimally invasive surgeries where a surgeon's vision may be obscured or limited.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after being placed on the heart. Systems for securing the opposing edges are disclosed in, for example, U.S. Pat. No. 5,702,343, the entire disclosure of which is incorporated herein by reference.

Figure 3A:
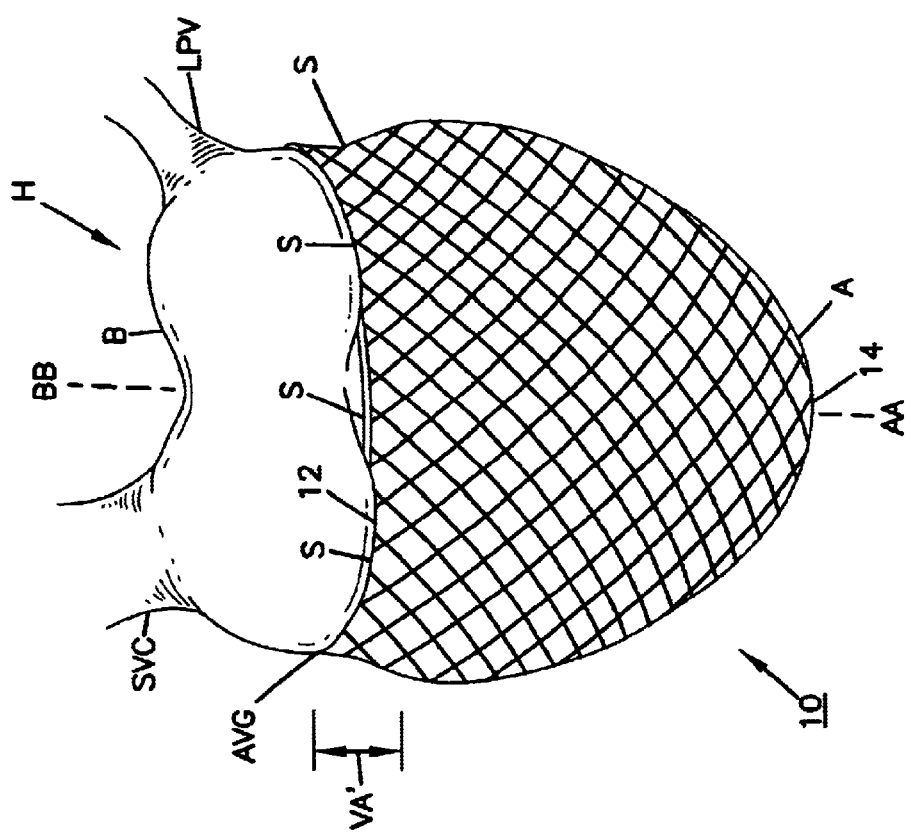
FIG. 3A is a side elevation view of a diseased heart in diastole with the device of FIG. 3 in place.
Figure 3:
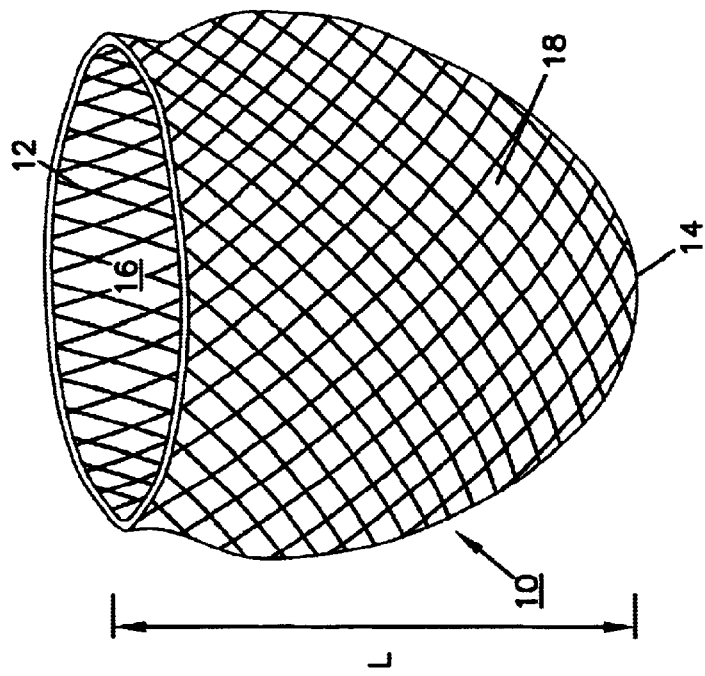
FIG. 3 is a perspective view of a first embodiment of a cardiac constraint device according to the present invention.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10'. Such placement is desirable for the jacket 10, 10' to present a constraint against enlargement of the ventricular walls of the heart H.

After the jacket 10 is positioned on the heart H as described above, the jacket 10 is secured to the heart. Preferably, the jacket 10 is secured to the heart H through sutures or other suitable surgical attachment methods. The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

In another embodiment, the jacket is secured to the heart using a suitable bioadhesive. The bioadhesive can be used in connection with a jacket alone, or in combination with one or more therapeutic agents and/or a nonadherent material. As used herein, a "bioadhesive" means a material that adheres an element to a biological tissue, or two biological tissues to each other. Preferably, the bioadhesive is fabricated from a material that is biologically compatible and allows secure attachment to a tissue. According to the present invention, preferred bioadhesives attach the jacket 10 to the heart in a sufficient non-shifting manner and for a sufficient amount of time to allow the desired effects. The bioadhesive preferably secures the jacket sufficiently to avoid dislocation of the jacket as a result of the heart's natural movement. Preferred bioadhesives are thus somewhat flexible to accommodate movement of the heart or surrounding tissue.

Preferably, bioadhesives used in accordance with the invention do not cause undesired adverse effects, such as irritation, inflammation, infection, and the like, of tissues of the heart and/or in proximity thereto. Preferably, when the jacket is used in connection with a bioadhesive, suitable bioadhesives do not interfere with penetration of a therapeutic agent from the device into the myocardium. In one embodiment, areas of the device that include one or more bioadhesives are separate from areas that include one or more therapeutic agents. Alternatively, areas of the device that include one or more bioadhesives overlap areas that include one or more therapeutic agents. In this alternative embodiment, the bioadhesive is preferably permeable to the therapeutic agent, so that the bioadhesive does not interfere with release of the therapeutic agent to the surface of the heart. In yet another embodiment, the bioadhesive itself includes one or more therapeutic agents.

Preferred bioadhesives are fabricated from such materials as polyethylene glycol, fibrin, cyanoacrylate, or material comprising a combination of bovine serum albumin (BSA) and gluteraldehyde. Suitable polyethylene glycol-based materials are provided by Focal, Inc., under the product name Focal Seal™, and Cohesion Technologies, Inc. under the product name CoSeal™. Examples of fibrin-based materials are provided by Haemacure Corporation under the product name Hemaseel™. Suitable material based in combining bovine serum albumin and gluteraldehyde are provided by Cryolife International, Inc. Examples of cyanoacrylate-based materials are provided by Johnson & Johnson under product name Dermabond™. Other suitable bioadhesives known in the art could be substituted for the above materials, given the description herein.

Figure 5:
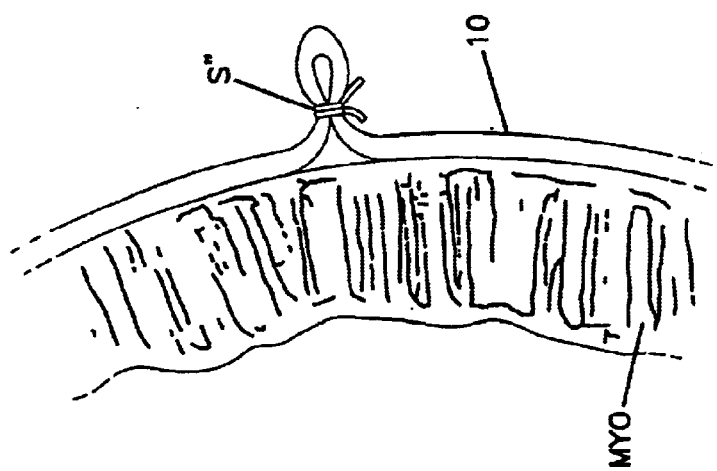
FIG. 5 is a cross-sectional view of a device of the present invention overlying a myocardium and with the material of the device gathered for a snug fit.
Figure 10:
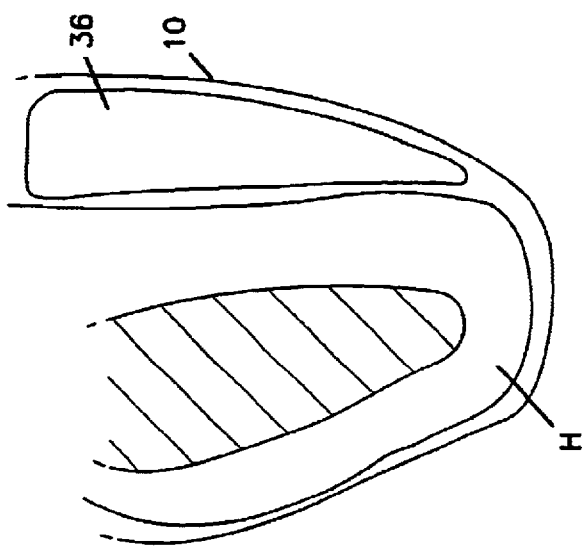

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. Preferably, the flexible material of the jacket allows unrestricted filling of the heart during diastole. As an alternative to gathering of FIG. 5, the jacket 10 can be provided with other ways of adjusting volume. For example, as disclosed in U.S. Pat. No. 5,702,343, the jacket can be provided with a slot. The edges of the slot can be drawn together to reduce the volume of the jacket.

The volume of the jacket can be adjusted prior to, during, or after application of the device to the heart. In one embodiment, the heart is treated with a therapeutic agent, such as a drug, to decrease the size of the heart prior to application of the jacket. In this embodiment, the therapeutic agent acts to reduce the overall size of the heart prior to surgery, and the jacket is thereafter applied to the reduced heart. In another embodiment, the size of the heart is reduced by placement of the device on the heart, and sizing of the device to urge the heart to a reduced size. More preferably, the heart size can be reduced at the time of jacket placement through drugs, for example dobutamine, dopamine or epinephrine or any other positive inotropic agents. Alternatively, surgical procedure can be used to reduce the heart size. The jacket of the present invention is then snugly placed on the reduced sized heart and prevents or reduces enlargement beyond the reduced size.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

Figure 6:
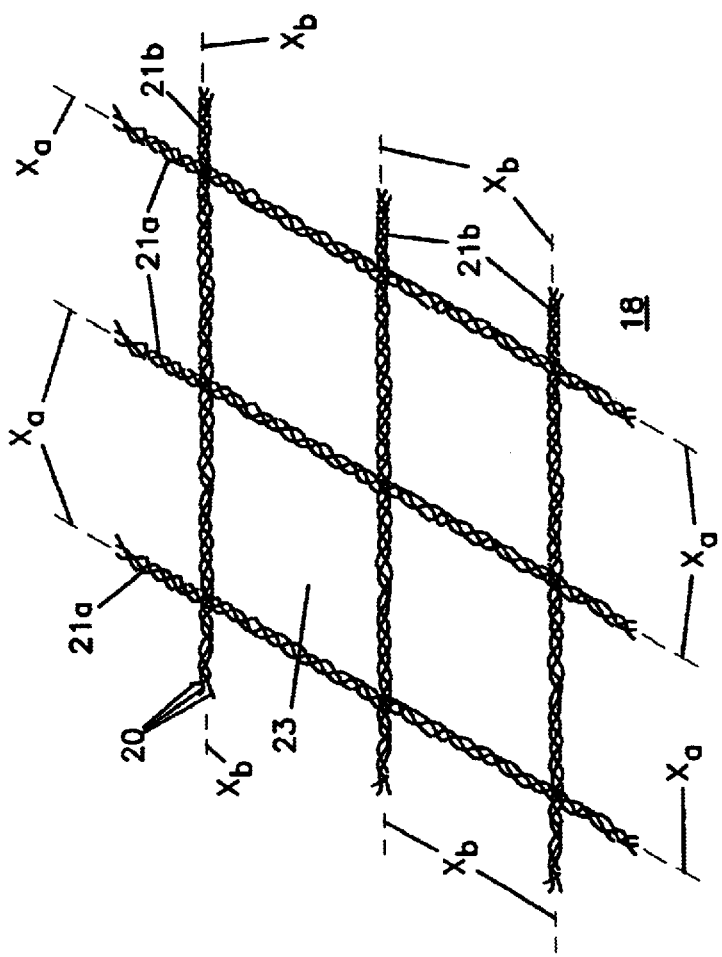
FIG. 6 is an enlarged view of a knit construction of the device of the present invention in a rest state.

The jacket 10 is constructed from a knit, biocompatible material. The knit 18 is illustrated in FIG. 6. Preferably, the knit is a so-called "Atlas knit" well known in the fabric industry. The Atlas knit is described in Paling, *Warp Knitting Technology*, p. 111, Columbine Press (Publishers) Ltd., Buxton, Great Britain (1970).

The Atlas knit is a knit of fibers 20 having directional expansion properties. More specifically, the knit 18, although formed of generally inelastic fibers 20, permits a construction of a flexible fabric at least slightly expandable beyond a rest state. FIG. 6 illustrates the knit 18 in a rest state. The fibers 20 of the fabric 18 are woven into two sets of fiber strands 21a, 21b having longitudinal axes $X_a$ and $X_b$. The strands 21a, 21b are interwoven to form the fabric 18 with strands 21a generally parallel and spaced-apart and with strands 21b generally parallel and spaced-apart.

Figure 7:
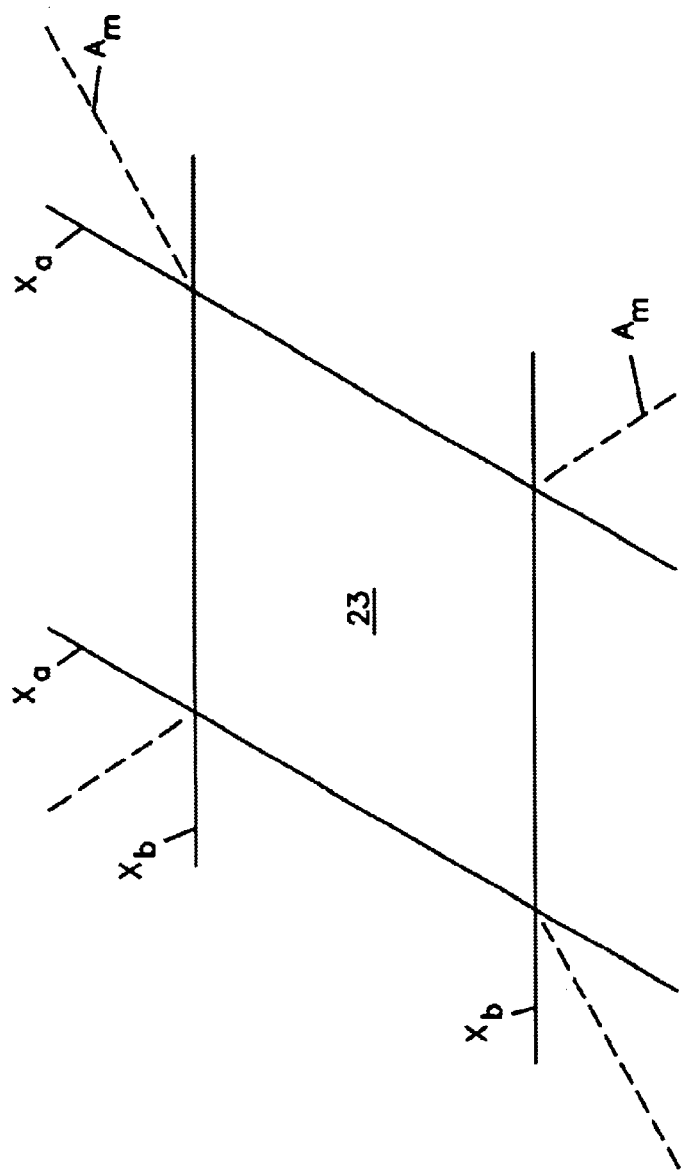
FIG. 7 is a schematic view of the material of FIG. 6.

For ease of illustration, fabric 18 is schematically shown in FIG. 7 with the axis of the strands 21a, 21b only being shown. The strands 21a, 21b are interwoven with the axes $X_a$ and $X_b$ defining a diamond-shaped open cell 23 having diagonal axes $A_m$. In a preferred embodiment, the axes $A_m$ are 5 mm in length when the fabric 18 is at rest and not stretched. The fabric 18 can stretch in response to a force. For any given force, the fabric 18 stretches most when the force is applied parallel to the diagonal axes $A_m$. The fabric 18 stretches least when the force is applied parallel to the strand axes $X_a$ and $X_b$. The jacket 10 is constructed for the material of the knit to be directionally aligned for a diagonal axis $A_m$ to be parallel to the heart's longitudinal axis AA–BB.

While the jacket 10 is expandable due to the above described knit pattern, the fibers 20 of the knit 18 are preferably non-expandable. While all materials expand at least a small amount, the fibers 20 are preferably formed of a material with a low modulus of elasticity. In response to the low pressures in the heart H during diastole, the fibers 20 are essentially non-elastic. In a preferred embodiment, the fibers are 70 Denier polyester. While polyester is presently preferred, other suitable materials include polytetrafluoroethylene (PTFE), polypropylene, stainless steel, and the like. Alternatively, the fibers of the jacket are fabricated from a suitable biodegradable material or blends thereof, as described herein.

The knit material has numerous advantages. Such a material is flexible to permit unrestricted movement of the heart H (other than the desired constraint on cardiac dilation). The material is open, defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allow for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

In one preferred embodiment, the interstitial spaces of the knit construction contain the therapeutic agent of the present invention. For example, in one embodiment, the interstitial spaces are filled with a biodegradable space fill material comprising a biologically compatible and/or biodegradable polymer matrix containing the therapeutic agent, as discussed in more detail below.

A large open area for cells 23 is desirable to minimize the amount of surface area of the heart H in contact with the material of the jacket 10 (thereby reducing fibrosis). However, if the cell area 23 is too large, localized aneurysm can form. Also, a strand 21a, 21b can overlay a coronary vessel with sufficient force to partially block the vessel. A smaller cell size increases the number of strands thereby decreasing the restricting force per strand. In a preferred embodiment, the cell area CA of cells in a particular row directly correlates with a cross-sectional circumferential dimension of the heart that the row of cells surrounds relative to other cross-sectional circumferential dimensions. That is, the greater the cross-sectional circumferential dimension, the greater the area of the cells in the row of cells directly overlying that cross-sectional circumferential dimension. By "correlating" cell area with cross-sectional circumferential dimension of the heart, the cell area is determined as a function of the cross-sectional circumferential dimension of the heart. The cell area is determined so that when the weave material is applied to the heart or is shaped into a jacket and applied to the heart, each cell can widen sufficiently to provide desirable cardiac constraint. Thus, the cell area will be smaller for cells in a row applied over a region of the heart that has a smaller cross-sectional circumferential dimension than the cell area of cells in a row applied over a region of the heart having a larger cross-sectional circumferential dimension. The appropriate maximum cell area may be, for example, 1 to 100 mm$^2$, typically 3 to 9 mm$^2$. The maximum cell area is the area of a cell 23 after the material of the jacket 10 is fully stretched and adjusted to the maximum adjusted volume on the heart H as previously described.

The fabric 18 is preferably tear and run resistant. In the event of a material defect or inadvertent tear, such a defect or tear is restricted from propagation by reason of the knit construction.

In an alternative embodiment, the jacket is fabricated from an elastic material. A biologically compatible material suitable for a device of the invention generally has a lower compliance than the heart wall. Even though the biologically compatible material is less compliant that the heart wall, some limited expansion of an elastic biologically compatible material can occur during cardiac filling. Suitable elastic materials for jacket fabrication include, for example, polyurethane, silicone, and the like.

Regardless if the biologically compatible material is elastic or non-elastic, advantageous to a device according to the present invention is cardiac reinforcement which is provided during diastole. Moreover, a device as disclosed herein does not provide cardiac assistance through active pumping of the heart.

A device and method to treat cardiac disease have been disclosed in U.S. Pat. No. 5,702,343 (commonly assigned to the assignee of the present invention, and the disclosure of which is incorporated herein by reference). The jacket 10 constrains further undesirable enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE, polyethylene glycol, polyethylene oxide, or other polymer coating on the fibers of the knit) could be used with the jacket 10, for example, between the heart and the jacket, or applied on the outer surface of the jacket (away from the heart). Alternatively, the fibers 20 can be coated with PTFE.

In one embodiment, a non-adherent material is provided in connection with the jacket 10 of the invention, to prevent unwanted fibrosis as a result of the presence of the jacket on the surface of the heart. As used herein, "non-adherent material" means a material that is biocompatible and does not adhere to surfaces of organs, such as the epicardial surface of the heart. The material can be preformed in a manner similar to the jacket of the invention, as described above. In one embodiment, the non-adherent material is fabricated as part of the jacket of the invention. Alternatively, the non-adherent material is fabricated as a separate element of the invention, and is positioned between the jacket of the invention and the epicardial surface of the heart. The non-adherent material facilitates removal of the jacket, which can become difficult when the jacket has been in place on the heart for a long period of time.

In another embodiment, the non-adherent material is placed on the outer surface of the jacket; that is, the surface of the jacket facing away from the heart. In this embodiment, the non-adherent material prevents unwanted fibrosis of or adhesions to surrounding tissues. Alternatively, the non-adherent material can be configured to be a hydrogel material that fills interstitial spaces of the jacket. It will be apparent to one of skill in the art that the non-adherent material can be configured to prevent undesirable fibrosis or other damage to any target tissue.

The non-adherent material can be adapted to cover any desired surface of the heart, such as the entire surface of the heart, or selected areas of the heart only. In one embodiment, the material can be fabricated to line the entire jacket, thus covering the entire epicardial surface of the heart that would otherwise be in contact with the jacket.

Figure 8:
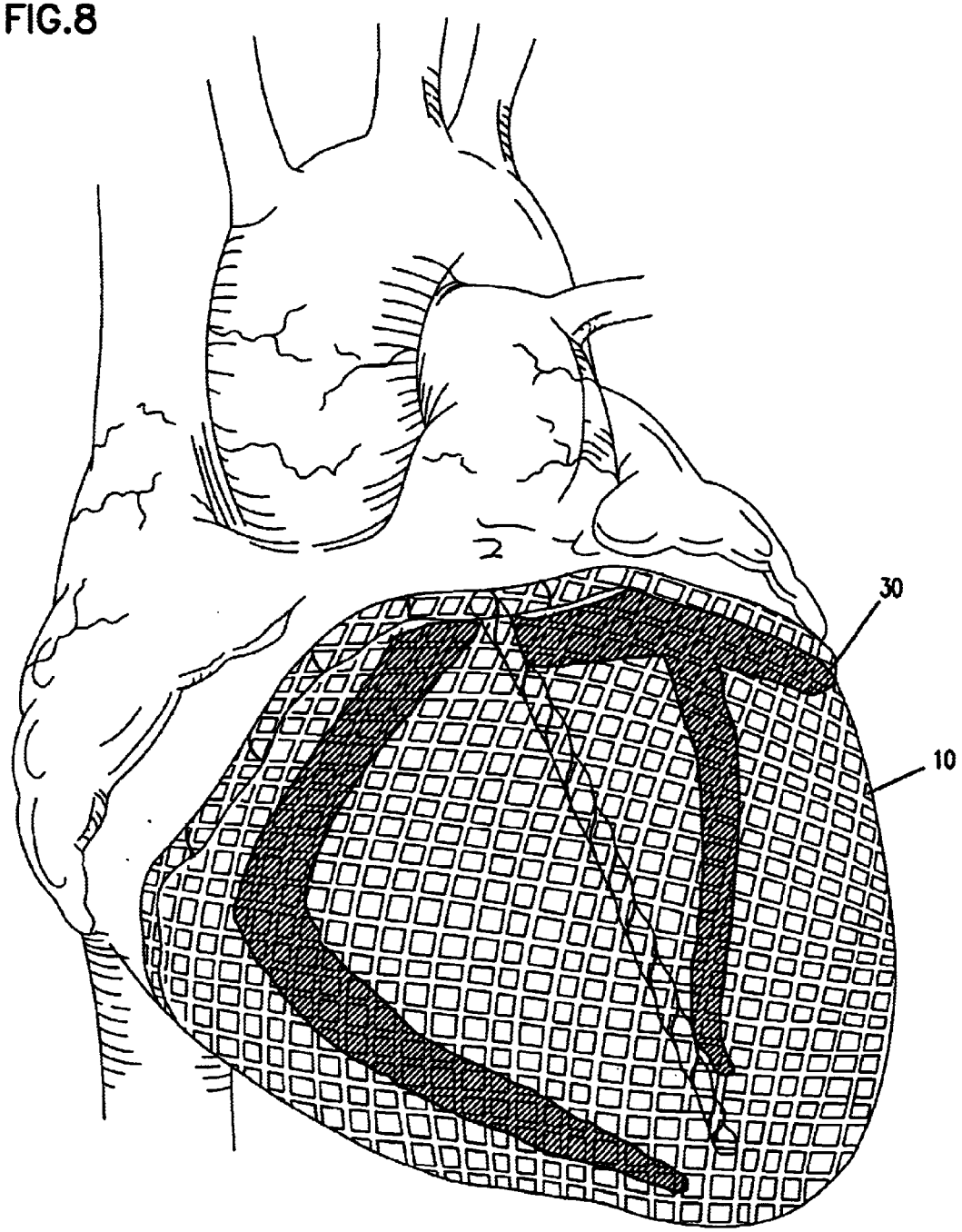
FIG. 8 is a perspective view of an embodiment of a cardiac reinforcement device according to the invention, including non-adherent biocompatible material placed between the jacket and the myocardium.

Removal of the jacket at selected sites may be required to access the coronary arteries in order to form an anastemotic site for coronary artery bypass in patients who received the device of the invention but subsequently develop coronary artery disease requiring bypass. Placement of non-adherent material at these selected sites facilitates removal of the jacket and access to these arteries. In one embodiment shown in FIG. 8, the non-adherent material 30 is placed at strategic sites between the jacket 10 and the epicardial surface of the heart, to allow access to the coronary vessels. For example, the non-adherent material is placed to cover only the epicardial course of the major coronary arteries. This will allow a surgeon to remove part of the jacket if coronary artery bypass surgery is deemed necessary in a patient who received the device of the invention in the past.

Figure 9:
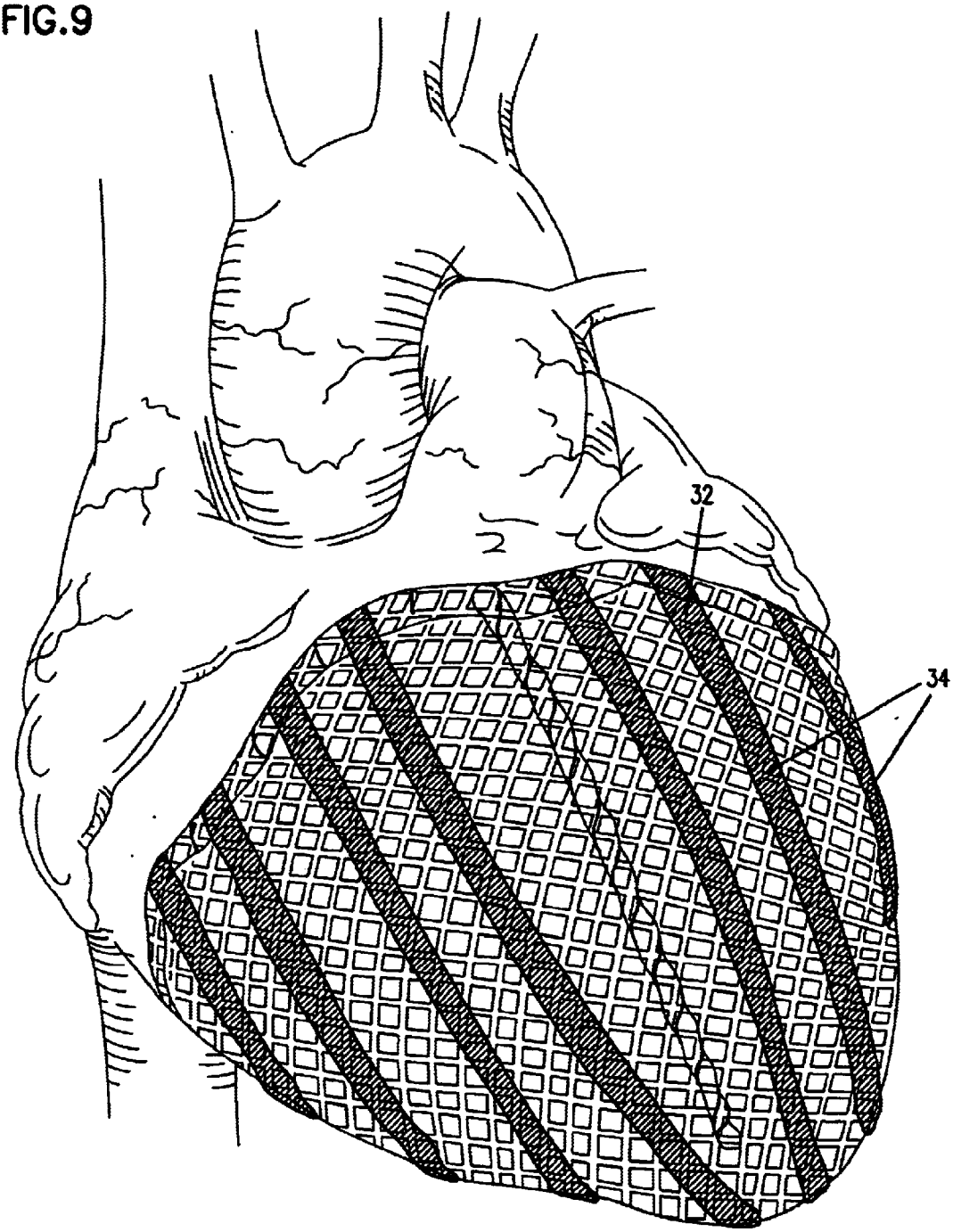
FIG. 9 is a perspective view of an embodiment of a cardiac reinforcement device according to the invention, including non-adherent biocompatible material in the form of ribs in association with the jacket.

Alternatively, the non-adherent material is placed at strategic base-to-apex locations to allow relief of constriction. In one embodiment shown in FIG. 9, the non-adherent material 32 preferably forms ribs 34 that course from base to apex of the heart. Preferably, the ribs are provided a finite distance apart along the device. This embodiment is desirable should the jacket cause constriction of the heart. The ribs allow the surgeon to score the jacket at the rib sites in the event a patient develops a constrictive or restrictive pattern as a result of the jacket. Relief of constriction is desirable in certain patients. For example, constrictive physiology may occur in some patients as a result of the presence of the jacket and pressure of the heart during diastole. This may in turn require removal of the jacket.

The non-adherent material is fabricated from any suitable material that provides the desired properties. In one embodiment, the non-adherent material is fabricated from the same material used to fabricate the jacket 10, for example, polyesters, PTFE, polypropylene, polyurethane, silicone, and the like. In yet another embodiment, the non-adherent material is fabricated from a different material than the jacket 10. Another example of suitable non-adherent material is available commercially under the brand name GORE-TEX™. In yet another embodiment, the non-adherent material is fabricated from a hydrogel, as described herein. The non-adherent material can be flexible or rigid, depending upon the desired application. Given the present teaching, one of skill in the art can select a suitable non-adherent material.

The non-adherent material is provided, in one embodiment, as a separate element of the device. For example, the non-adherent material can be provided as a separate lining that is placed between the jacket and the surface of the heart, or on the outside surface of the jacket, facing away from the heart. In yet another embodiment, the non-adherent material of the invention is provided as a coating on -the jacket of the device.

The device of the invention can include non-adherent material and can optionally further include antifibrotic agents, if desired. Placement of the non-adherent material, when provided as a separate element of the device, is accomplished at any suitable time during application of the jacket, for example, prior to, during, or after placement of the jacket on the heart. When provided as a separate element of the device, the non-adherent material is held in place on the heart surface by the jacket 10. In this embodiment, the snug fit of the jacket 10 is sufficient to maintain the desired location of the non-adherent material on the heart. Alternatively, the non-adherent material is attached to the jacket 10. In this alternative embodiment, attachment of the non-adherent material to the jacket, and the attachment of the jacket 10 to the heart (as discussed supra) maintains placement of the non-adherent material. Securement of the non-adherent material to the jacket can be accomplished using any suitable means, such as, for example, sutures, staples, bioadhesives, or the like. Given the description herein, one of skill in the art can readily choose suitable methods for securing the non-adherent material to the jacket.

The non-adherent material can be fabricated to be permeable to therapeutic agents, so that the material does not interfere with delivery of the agent(s) to the heart. Alternatively, the non-adherent material is impermeable to therapeutic agent(s), for example, when there is no concern with interference of delivery of the therapeutic agent(s), such as when the location of the non-adherent material is separate from the location of any therapeutic agents included in the device.

The jacket 10 is low-cost, easy to place and secure, and is amendable to use in minimally invasive procedures. The thin, flexible fabric 18 permits the jacket 10 to be collapsed and passed through a small diameter tube in a minimally invasive procedure.

The jacket 10 can be used in early stages of congestive heart failure, such as myocardial infarction or congestive heart failure, or late stages, such as chronic dilated cardiomyopathy. For patients facing cardiac enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

The jacket 10, including the knit construction, freely permits longitudinal and circumferential contraction of the heart H (necessary for heart function). Unlike a solid wrap (such as a muscle wrap in a cardiomyoplasty procedure), the fabric 18 does not impede cardiac contraction. After fitting, the jacket 10 is inelastic to prevent further heart enlargement while permitting unrestricted inward movement of the ventricular walls. Further, the jacket permits unrestricted diastolic filling of the heart. The jacket prevents overstressing or stretching of the ventricle at the end of diastole. The open cell structure permits access to coronary vessels for bypass procedures subsequent to placement of the jacket 10. Also, in cardiomyoplasty, the latissimus dorsi muscle has a variable and large thickness (ranging from about 1 mm to 1 cm). In contrast, the material of the jacket 10 is uniformly thin (less than 1 mm thick). The thin wall construction thus reduces the risk of fibrosis and minimizes interference with cardiac contractile function.

Animal test studies on the jacket of the invention show the efficacy of the jacket of the present invention. Test animals were provided with the device 10 of FIG. 3. The animals' hearts were rapidly paced to induce heart failure. After six weeks, animals without the device experienced significant heart enlargement while those with the device experienced no significant enlargement. Further, animals with the device had significantly reduced mitral valve regurgitation and had improved contractability as measured by ejection fraction.

The jacket described above is used in connection with a delivery source for the delivery of a therapeutic agent to the surface of the heart. As used herein, a "therapeutic agent" is an agent that assists in the treatment, cure, relief or prevention of disease or disorders of the heart or surrounding tissue. Therapeutic agents function by affecting the structure or function of the tissue treated, to have the desired effect.

The present invention provides a device and method for localized, targeted delivery of a therapeutic agent to a target area of the heart and/or of surrounding tissues. As used herein, "target," "target area" and "target tissue" refer to a selected site of the heart, or of tissues surrounding the heart, intended to be treated using the present invention. As contemplated in the present invention, the target tissue can comprise any desired area to be treated with a method or device of the invention, including, for example, a specific area of the heart (such as an area of ischemia or necrosis, or one or more diseased or damaged arteries), the entire surface of the heart, or selected tissues surrounding the heart (such as the lung or pericardium). Further, after delivery to the surface of the target tissue, such as the heart, the therapeutic agent can penetrate the tissue surface and thereby act below the surface of the tissue.

As contemplated in the present invention, therapeutic agents include one or more pharmacological agents, cellular material, and/or combinations thereof. While the present application provides examples of suitable therapeutic agents, the disclosure hereof should not be interpreted to be so limited. The discussion of particular exemplary therapeutic agents herein is not meant to be limiting; rather, the disclosure should be interpreted to encompass suitable therapeutic agents within the scope of the invention.

Suitable pharmacological agents include chemicals or pharmacological compounds that affect the target tissue, such as the heart and/or surrounding tissues, and its processes. Examples of suitable pharmacological agents include anti-arrhythmic drugs, thrombolytic agents, anti-restenotic agents, anti-inflammatory or anti-fibrotic agents, anti-apoptotic agents, antibiotics, neurohormone inhibitors, antineurohormone agonists, leukocyte inhibitory factor antagonists, glycoprotein 130 antagonists, anti-immune rejection agents, inhibitors of matrix metalloproteinases, agents that prevent calcification, agents that increase intracellular calcium without activating $\beta$-adrenergic receptors, metabolic factors, nucleic acid molecules, and other comparable agents capable of treating, curing, relieving or preventing disease or disorders in target tissues.

As contemplated by the present invention, anti-arrhythmic drugs are compounds that act to inhibit arrhythmia (that is, abnormal cardiac rhythm) and stabilize normal sinus rhythm to the heart. Examples of anti-arrhythmic drugs include those classified as type I (such as lidocaine, procainamide, encainide, flecainide), type II (for example, $\beta$-adrenergic blocking agents such as norepinephrine, epinephrine, isoproterenol, propanolol, dobutamine), and type III (such as ibutilide and solatol), as well as quinidine, phenytoin, angiotensin converting enzyme (ACE) inhibitors, nitroglycerin, hydralazine, captopril, and calcium channel blockers such as verapanil, nifedipine, and diltiazem.

Thrombolytic agents are compounds that act to dissolve or split up clots in the body. Examples of suitable thrombolytic agents include streptokinase, urokinase, tissue plasminogen activator (TPA), and the like.

In another embodiment, the therapeutic agent of the present invention comprises one or more anti-restenotic agents. As used herein, anti-restenotic agents are agents that inhibit restenosis (i.e., cell proliferation) and/or extracellular matrix synthesis at the level of atherosclerotic plaque, of coronary arteries following percutaneous translumenal coronary angioplasty, or vascular grafts following coronary artery bypass grafting procedures. Examples of suitable anti-restenotic agents include anti-thrombotic agents (such as heparin and ReoPro), and radionuclide emitters, and the like.

Alternatively, the therapeutic agent of the present invention comprises one or more anti-inflammatory or anti-fibrotic agents. Such anti-inflammatory or anti-fibrotic agents are agents that inhibit scar formation associated with aberrant fibrosis and prevent formation of epicardial fibrosis, which could interfere with diffusion of other agents from the device of the present invention to the target tissue and could increase resistance to electric current flow, thus requiring a pacemaker to deliver more voltage. Examples of suitable anti-inflammatory or anti-fibrotic agents include steroids, such as dexamethasone and the like, and lathrogenic agents such as penicillamine, n-acetyl-cysteine, $\beta$-aminopropionitrile, and the like.

In another embodiment, the therapeutic agent is provided in the form of a metabolic effector. As used herein, a metabolic effector represents a biologically active molecule that is capable of altering activity in a metabolic pathway. Thus, a metabolic effector is able to alter biological response elicited by intermediates, or final products of a metabolic pathway. Such effectors may be enzymes, enzyme inhibitors or stimulators, neurohormones, hormones, and the like. Examples include natural and pharmaceutical agents intended to serve as antagonists or agonists, with specific binding activity to enzymes involved in neurohormone metabolism, or cell membrane-bound receptors of such neurohormones. Among these metabolic effectors are ACE inhibitors, which inhibit angiotensin converting enzyme and metabolic conversion of angiotensin I to angiotensin II, thiorphan, which inhibits neutral endoprotease and prevents metabolic breakdown of atrial natriuretic peptide, spironolactone, $\beta$-blockers, and losartan. These latter three effectors are antagonists of aldosterone, catecholamines (such as norepinephrine), and angiotensin II, respectively, and thus inhibit receptor binding, and biological response normally elicited by these natural metabolites.

Alternatively, the therapeutic agent can be provided in the form of a therapeutic gene that functions to assist in the treatment, cure, relief or prevention of disease or disorders of the heart or surrounding tissue. As used herein, a "therapeutic gene" is a segment of nucleic acid that specifies a particular protein or polypeptide chain that, when expressed, provides a therapeutic effect. Many such therapeutic genes are known in the art to provide beneficial effects in the treatment of cardiac disease or disorders. For example, suitable therapeutic genes function to prevent restenosis, promote angiogenesis, modulate pathways of electrical conductance to control cardiac arrhythmias, enhance the wound healing process (for example, using such growth factors as TGF-$\beta$), or express thrombolytic agents such as tissue plasminogen activator (TPA) or urokinase.

In this embodiment, the therapeutic agent comprises one or more gene agents, such as naked gene plasmids, oligonucleotides, ribozymes, and viral vectors containing genes encoding specific transgene products. Such gene agents provide mechanisms for introducing genes into the target area, to promote expression of a transgene product.

When provided in the form of nucleic acid, the therapeutic agent can be provided through a delivery system, such as liposomes, microspheres, nanospheres, and polymer matrices, or may be provided as naked nucleic acid. When provided with a polymer matrix, the nucleic acid can be either entrapped or dispersed into the polymer matrix or adsorbed onto the surface. Polymers can be provided as biodegradable materials such as polyesters or polyanhydrides or blends thereof; nonbiodegradable materials such as ethylene vinyl acetate copolymers; or natural materials such as collagen or gelatin.

Suitable pharmacological agents can be surface-acting or can penetrate the myocardium. For example, small molecule compounds are capable of penetrating the myocardium to act beneath the surface of the heart. Examples of small molecule compounds that are capable of penetrating the MYO include anti-arrhythmic agents, lathrogenic agents, such as penicillamine, N-acetyl-L-cysteine, and 3-aminoproprionitrile fumarate, and the like.

When the therapeutic agent comprises a pharmacological agent, the agent can be provided with any suitable carrier diluent, filler, binder or other excipient, depending upon the composition of the delivery source and the dosage desired, for delivery of the agent to the target tissue. By "carrier" is meant a pharmaceutically acceptable carrier that is conventionally used in the art to facilitate the storage, administration, and/or healing effect of the agent. A carrier may also reduce any undesirable side effects of the agent. A suitable carrier should be stable, i.e., incapable of reacting with other ingredients of the formulation. It should not produce local adverse effects in recipients at the dosages and concentrations employed for treatment. Such carriers are generally known in the art. See *Remington's Pharmaceutical Sciences*, 16$^{th}$ edition, Olso, A. ed. (1980).

In another embodiment, the therapeutic agent of the present invention is provided in the form of cellular material. As contemplated in the present invention, cellular material means material that is obtained from differentiated cells with a different phenotype (such as smooth muscle cells, endothelial cells, and fibroblasts) or with the same phenotype (such as myocardial cells). Alternatively, the cellular material is obtained from non-differentiated cells, such as mesenchymal cells. Cellular material is introduced to the heart to repair, replace or enhance the biological function of damaged cells in order to strengthen a weakened heart. Suspensions of cellular material can be injected into diseased cardiac tissue, and the implanted cells become important contributors towards normalization of structure and function of diseased tissue. In one preferred embodiment, cellular material is injected into the myocardium, which leads to incorporation of the cells into the tissue, cell contraction synchronous with adjacent cells, and an improvement in cardiac hemodynamics. Cellular material includes myogenic cells, endocrine cells, islet cells, and any other suitable cell type desired for application using the invention described herein.

The cells may be of a single tissue type or may contain a mixed population of cells. The cell culture may include cells that are xenogenic, allogenic and/or isogenic to the host in which they are implanted. Propagation of vertebrate cells in culture is well known in the art (See, e.g., *Tissue Culture*, Academic Press, Kruse and Patterson, editors (1973)).

The implanted cellular material may include culture media. Those of-skill in the art are familiar with cell culture media. Examples of commercial available media include Ham's F10 (Sigma), Minimal Essential Medium ("MEM", sigma), RPMI-1640 (Sigma), and Dulbecco's Modified Eagle's Medium ("DMEM", Sigma). The media may be supplemented as necessary with hormone and/or other growth factors, salts, buffers, nuclosides, antibiotics and trace elements (inorganic compounds usually present at final concentrations in the micromolar range). Alternately, the delivery source may allow nutrients to diffuse into the cavity to support the live cell culture.

In one embodiment, the implanted cells produce a therapeutic agent that has a beneficial effect on the host. In this embodiment, the therapeutic agent can comprise one or more of the therapeutic agents discussed supra.

In one embodiment of the invention, the implanted cells can be genetically engineered transformed cells. As used herein, the term "transformed cells" refers to cells in which an extrinsic DNA or gene construct has been introduced such that the DNA is replicable, either as an extrachromosomal element or by chromosomal integration. Transformation of the cells is accomplished using standard techniques known to those of skill in the art and is described, for example, by Sambrook et al., *Molecular Cloning: A Laboratory Manual*, New York, Cold Spring Harbor Laboratory Press (1989).

Extrinsic DNA or gene construct refers to a nucleic acid sequence originating outside a recipient cell and introduced into a recipient cell by a DNA delivery technique. A DNA or gene construct may be manufactured using recombinant DNA technology known in the art, or may be a nucleic acid fragment purified from a source material. The extrinsic gene may be entirely composed of homologous sequence, i.e., sequences cloned, isolated, or derived from the same species from which the recipient cells derive. Alternatively, all or a portion of the extrinsic gene may be composed of sequences from species other than the species from which the recipient cells derive, hereinafter termed heterologous sequences. The extrinsic gene construct may be natural in that none of the regulatory sequences and coding sequences that may be a part of the gene are substantially or intentionally altered, or the extrinsic gene construct may be chimeric in that sequence fragments from various sources are present in the final gene construct.

In one embodiment, cellular material is selected from smooth muscle cells, endothelial cells, mesenchymal stem cells, and fibroblasts and is introduced into the cardiac environment using transdifferentiation. Transdifferentiation is a procedure such as that described by Kessler et all, that involves the conversion of a committed, differentiated, or specialized cell to another differentiated cell type with a distinctly different phenotype (See *Myoblast Cell Grafting Into Heart Muscle: Cellular Biology and Potential Applications*, P. D. Kessler et al., Annu. Rev. Physiol. 1999, 61:219–42). In the present invention, smooth muscle cells, endothelial cells, mesenchymal stem cells, and/or fibroblasts from a donor can be provided in connection with the delivery source (e.g., the cells can be seeded onto the surface of the delivery source, as discussed in more detail below), to provide a source of cellular material for transdifferentiation.

In another embodiment, the cellular material comprises myogenic cells that are grafted onto the surface of the heart. In this aspect, new myogenic cells, such as cardiomyocytes, are introduced into the myocardium for repair of the heart. As used herein, grafting includes coating or impregnating cardiomyocytes onto or within the delivery source for application to the surface of the heart, or injecting cardiomyocytes into the heart muscle through direct epicardial injection. Preferably, myogenic cells are harvested from the patient receiving treatment, to minimize rejection of the cells.

In one embodiment, the jacket material serves as a scaffold onto which the matrix material containing the therapeutic agent is attached. For example, contractile cells can be seeded or sodded into/onto the jacket in such a way that the jacket material serves as a scaffold for support of the cells. As described herein, the cells can be harvested from a patient culture and applied to the jacket material. Alternatively, mesenchymal cells can be harvested from another patient and applied to the jacket material. In either event, these cells can then be adapted to perform contractile work, much in the way that skeletal muscle is adapted to the requirements for contraction in association with cardiomyoplasty. Cells implanted on/in the jacket can be exposed to an oriented electric field in such a way that the cells orient into a contractile element. Optimally, the biocompatible material comprising the material of the jacket is itself designed and oriented in the proper direction(s) of muscle contraction (i.e., in line with muscle fibers of the heart). The cells contained on the device are then capable of being stimulated using an electronic pacemaker, synchronous with the heart. Approaches to replacing myocardial scar tissue with cardiac cells are discussed, for example, by Li et al., in *Cell Therapy to Repair Broken Hearts*, Can. J. Cardiol. 14, 5: 735–744 (1998).

Myocardial cells, or other viable cell population can be attached to the jacket by various specific and non-specific means. Cells can be cultured directly onto the fabric of the jacket. Under suitable circumstances, cells can be promoted to completely cover the jacket surface. In the case of myocytes, the cells can be made to contract synchronously, perhaps providing a synthetic active contractile element to support the heart. Attachment of cells to the jacket can be via a spacer arm covalently attached to the jacket backbone polymer. This spacer arm, typically consisting of a string of methylene groups, or natural or synthetic peptides, is structured to have a biologically active attachment group at its terminus, which would interact with a receptor on the cell surface. One example would be use of a poly-lysine peptide (or other such backbone) which terminates with an rgd (arginine-glycine-aspartic acid) sequence. The rgd sequence is known to bind with specific cell surface receptors, stabilizing attachment of cells. Similar examples have been used in construction of prosthetic vascular grafts, in which rgd peptides are incorporated into the graft to facilitate binding and stabilization of endothelial cells.

Cellular material introduced to the surface of the heart has a variety of clinical applications. For example, implanted cells can provide a platform for protein delivery at the surface of the heart. In this embodiment, cells provide a continual source of protein delivery at the surface of the heart to promote myocardial repair and to enhance growth of the transplanted cells. For example, myocytes can be altered genetically to deliver recombinant TGF-β1 or other effector to the heart. Additionally, neurotrophic factors and/or angiogenic factors, such as vascular endothelial growth factor or fibroblast growth factor, can be locally expressed to avoid the potentially harmful effects of systemic delivery of these proteins.

The delivery source of the invention can be provided in a variety of suitable forms. In one embodiment, the delivery source comprises a coating that is provided on, and/or impregnated into, the material of the jacket. Alternatively, the delivery source comprises a separable delivery source that is provided in association with the jacket.

In one embodiment, the delivery source is provided as a coating on, and/or impregnated into the material of, the jacket of the device. In this embodiment, the coating comprises a matrix material and one or more therapeutic agents. As used herein, the matrix material is a biologically and pharmacologically compatible and/or biodegradable material that can be adapted to include one or more therapeutic agents. Preferably, the matrix material is flexible and permeable to the therapeutic agent, to provide a suitable source for controlled release of the agent. Examples of suitable matrix materials include and polymeric matrix materials and hydrogels.

The coating can be applied to the jacket in any suitable fashion, using methods known in the art, e.g., by dipping, coating, spraying, or impregnating the coating onto the jacket. The porous, knit biocompatible jacket material, as described herein, is particularly well suited for application of the therapeutic agent by coating or impregnation. The coating can be provided on the fibers 20 that form fiber strands 21a and 21b of the knit jacket material only, or the coating can be provided as a uniform coating of both the fibers 20 and the open cells 23 of the jacket. The viscosity of the coating will determine whether the coating is provided as a coating of the fibers only or as a uniform coating of the fibers and open cells. Viscosity of the coating is determined by such factors as the percent solids of the coating, and the molecular weight of the polymer.

The knit material of the jacket provides numerous advantages in connection with the delivery source. In one embodiment, the coating is provided on the individual fibers that form fiber strands 21a and 21b of the knit jacket. As described above, the individual fibers are interwoven along axes $X_a$ and $X_b$. The interwoven fiber strands provide an increased surface area for coating, as compared to single fiber strands or strands that are provided in side-by-side arrangement. Also, coating along the fibers only maintains the open, interstitial spaces of the knit, which in turn provides advantages of the material mentioned above.

Alternatively, the coating is provided as a uniform coating that not only coats the fibers, but also fills the interstitial spaces of the jacket. In this embodiment, the overall surface area of the delivery source is further increased, as the coating is provided not only on the surfaces of the fibers of the jacket, but also fills the interstitial spaces defined by the fibers. The interstitial spaces serve as reservoirs for the coating, providing spaced-apart areas of concentrated coating containing the therapeutic agent. At the same time, the advantages of the jacket are maintained, such as the flexibility of the jacket and contact with the heart that is intimate and non-shifting.

Whether the coating is provided along the fiber strands only, or over both the fiber strands and open cells, the flexibility of the jacket is maintained. The directional expansion properties of the knit material allows the delivery source of the device to maintain intimate contact with the surface of the heart so that one or more therapeutic agents can be released directly to the surface of the heart and/or target tissue surrounding the heart. The coating itself is sufficiently flexible so that it does not fracture and fall or peel off the material, but rather expands along with the jacket material. Further, because the jacket surrounds the heart and expands along with the heart during its natural movement, the delivery source is maintained in intimate contact with the surface of the heart for prolonged periods of time. The device is not loosened by natural movement of the heart, and therefore delivery of one or more therapeutic agents that is intimate and non-shifting can be provided for prolonged periods of time.

The coating can be provided at any suitable location on the jacket, including a selected portion, or the entire surface area, of the jacket. For example, a portion of the jacket overlying an area of ischemia can be provided with suitable therapeutic agents in that selected area only, while anti-fibrotic agents can be provided on another selected area, or the entire area, of the jacket at the same time. The method of coating the jacket can be modified to achieve the desired coating area.

The coating on the jacket is provided in suitable thickness to provide an adequate dosage of the agent to achieve the desired effect, while controlling the release of the agent to the target tissue. Other factors influencing the thickness of the coating include the size of the therapeutic agent, release kinetics of the agent, and hydrophobicity or hydrophilicity of the agent versus the coating. At the same time, the coating is not provided in a thickness that would adversely affect the flexibility of the jacket material. For example, as the thickness of the coating increases, the mass that the heart is required to move during diastole increases. As a result, the thicker the coating, the less flexible the jacket becomes, and the greater the risk of fibrosis from the jacket. As presently contemplated, the final (total) thickness of the coating is generally in the range of approximately 0.5 mm to approximately 4 mm, preferably in the range of approximately 0.5 mm to approximately 2 mm, and optimally in the range of approximately 0.5 mm to approximately 1 mm. However, it is to be understood that the final thickness of the coating can be adjusted to any suitable thickness that provides the advantages and characteristics herein described. The coating can be formed by applying a single coating, or by applying multiple coatings to achieve a final desired thickness.

The matrix material of the coating is preferably a polymeric material or a hydrogel. Preferred polymeric materials are those that have a low degree of crystallization, and are biocompatible. In one embodiment, the polymeric matrix material is biodegradable. Examples of biodegradable polymers that can be used in this embodiment include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazens, polyhydroxybutyrates, polyhdyroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers, or combinations or mixtures of the above materials. The matrix material can also be provided in the form of a hydrogel. In this embodiment, the therapeutic agent(s) are released from the matrix by diffusion and/or degradation of the matrix material.

In an alternative embodiment, the polymeric matrix material is non-degradable, so that the matrix material remains part of the implanted device and is not broken down over time. Examples of suitable non-degradable materials include, for example, polyurethanes (such as polyether polyurethane), or silicone rubber materials (such as polydimethylsiloxane derivatives). In this embodiment, the therapeutic agent is released by diffusion of the agent through the matrix material.

Preferably, because both the degradable and non-degradable materials are intended to remain in the body for extended periods of time, these materials do not contain any leachable components that may be toxic to tissues.

Depending upon the desired softness and flexibility of the coating, and rate of release of the therapeutic agent, the amount and type of polymer can be varied to produce the desired result. For example, for a relatively soft and flexible polymer matrix, copolymers with a low Tg can be used, primarily the lactide/caprolactone copolymers.

Preferably, the polymeric material is provided with a solvent that is non-toxic and biocompatible. Examples of suitable solvents include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, dimethyl acetamide, tetrahydrofuran, caprolactam, decylmethylsulfoxide, oleic acid, and 1-dodecylazacycloheptan-2-one. One of skill in the art could readily determine the appropriate solvent for the polymeric matrix material, using such factors as crystallinity, hydrophilicty, hydrogen-bonding and molecular weight of the polymeric material.

Typical application of a coating of the invention is as follows. The therapeutic agent(s) to be applied to the jacket are dissolved in a suitable solvent, such as dimethyl acetamide. In one embodiment, the therapeutic agent is soluble in the solvent, and a homogenous solution of the polymer and drug are applied to the jacket. Alternatively, the drug is not soluble in the solvent, and a suspension or dispersion of the drug in the solvent will result. The matrix material is also dissolved in the solvent. The therapeutic agent solution and matrix material solution are mixed, preferably forming a homogenous solution, although the solution may form a non-homogenous suspension. In either embodiment, the solvent will dissipate and the polymer solidifies and entraps or encases the therapeutic agent within the solid matrix.

The matrix material/therapeutic agent solution is then applied to the jacket, for example, by dip coating or other suitable method. The coated jacket is removed from the solution and optionally dried. The jacket is dried, for example, in a vacuum oven, or may be air dried, to evaporate the solvent from the jacket. The result is a thin film of the matrix material/therapeutic agent.

After placement of the device on the surface of the heart, the therapeutic agent is released from the coating into adjacent tissues by diffusion through the pores of the matrix material, and/or polymeric matrix degradation mechanisms. The rate and extent of release of the therapeutic agent from the delivery source are controlled over a range of speeds and amounts. Release of the therapeutic agent from the solid matrix will follow the same general rules for release of a therapeutic agent, such as a drug, from a monolithic polymeric device. Additionally, when the matrix material comprises a hydrogel polymer, the matrix material can be fabricated so that it swells in an aqueous environment, such as the body. In this embodiment, the hydrophilicity of the hydrogel can be altered (for example, by altering the polarity of the matrix material) to permit the desired water uptake. Such swelling of the matrix provides communication between the matrix and the adjacent tissues for delivery of a therapeutic agent.

Factors influencing the release rate include characteristics of the therapeutic agent, and characteristics of the overall coating. Characteristics of the therapeutic agent that influence release rate include water solubility, distribution within the matrix, concentration within the coating, chemical nature of attachment to the matrix material (i.e., chemical bond, if any), molecular weight, hydrophilicity or hydrophobicity, physical form, and the like. For example, release of a therapeutic agent having a low solubility in water, such as a lipid or other hydrophobic molecule, typically requires the degradation of a substantial part of the polymeric matrix to expose the material directly to the surrounding target tissue fluids.

The release rate is also influenced by characteristics of the overall coating that comprises a matrix material and therapeutic agent. For example, the polymeric matrix can be formulated to degrade after an effective and/or substantial amount of the therapeutic agent is released from the matrix. The release rate can be affected by the size and shape of the coating; material type and molecular weight of the matrix material; solubility, biodegradability, and/or hydrophilicity of the coating; permeability factors involving the therapeutic agent and the particular matrix material; degradation of the matrix; and the concentration and kinds of other additives present, if any, within the coating. Depending upon the therapeutic agent selected for use in the invention, the above parameters can be adjusted to give the desired rate and duration of release.

Generally, the thicker the coating, the greater the coating volume, and thus the amount of agent that can be incorporated into the coating. Consequently, a greater amount of a therapeutic agent can ostensibly be delivered from a thicker coating, and delivery can be tailored to occur over a greater time course. Other factors can influence delivery rate. Porosity in the coating, reflecting coating composition and density, can impact the ease of movement of therapeutic agents from the coating into adjacent cardiac tissue. Coating composition and chemical structure of the therapeutic agent or agents can influence the nature of interaction between these materials. If the therapeutic agent exhibits strong interaction with the coating, then the rate of release will be slow. For example, a polyurethane matrix coating containing hydrophilic moieties can be fashioned to provide a rapid release vehicle for hydrophilic therapeutic agents. Likewise, a hydrophobic therapeutic agent will have slow release kinetics from a hydrophobic polymer coating.

Optionally, the matrix material is formulated to provide an initial burst effect. This results in a bolus dose of the therapeutic agent, followed by a relatively constant release of the agent over time. Factors contributing to a greater initial burst include the thickness of the coating, the particle size of the therapeutic agent, and amount of therapeutic agent included in the coating. For example, factors contributing to a greater initial burst include greater thickness of the coating, larger particle size of the therapeutic agent, and higher amount or concentration of the therapeutic agent.

The present invention provides a device that is capable of delivering a range of doses of therapeutic agent over prolonged periods of time. The amount of therapeutic agent incorporated into the coating is determined by the patient's physician. This amount depends upon such factors as the desired release profile, concentration of the drug required for a therapeutic effect, and length of time that the therapeutic agent has to be released for effective treatment. For example, a coating containing a higher weight percent of therapeutic agent will generally release a higher total amount of therapeutic agent to the target tissue. According to the invention, the coating contains approximately 1% (by weight) to approximately 40% (by weight) of the therapeutic agent. Preferably, the coating contains approximately 5% (by weight) to approximately 30% (by weight) of the of the therapeutic agent, more preferably, approximately 10% (by weight) to approximately 15% (by weight).

In one embodiment, as the polymeric matrix degrades, the therapeutic agent is released from the delivery source. The delivery source will release the therapeutic agent within the matrix at a controlled rate until the therapeutic agent is depleted. With certain therapeutic agents, the polymer will degrade after the agent has been completely released. With other therapeutic agents such as peptides or proteins, the agent will be completely released only after the polymer has degraded to a point where the non-diffusing drug has been exposed to the body fluids.

In one embodiment, the matrix material of the coating is provided in the form of a hydrogel polymer. In this embodiment, the hydrated polymer matrix allows controlled release of the therapeutic agent to the target tissue. As discussed supra, the thickness of the hydrogel is controlled to vary the rate of release of the therapeutic agent. In contrast, when rapid release of the agent is desired, the thickness of the hydrogel is decreased. The ratio of therapeutic agent to hydrogel polymer in the matrix is adjusted to provide the desired release rate and dosage over time. Preferably, the hydrogel comprises at least 80% (v/v) water.

The hydrogel polymer is selected from polycarboxylic acids, water-swollen cellulose derivatives, gelatin, polyvinylpyrrolidone, maleic anhydride polymers, polyamides, poly(vinyl alcohol), polyethylene oxides, poly (2-hydroxyethyl methacrylate), poly(ethylene oxide), and copolymers thereof.

In one embodiment, the hydrogel polymer is characterized by the ability to incorporate a substantial amount of the therapeutic agent, typically in aqueous form, and is swellable such that the aqueous therapeutic agent solution can be effectively squeezed out of the coating when pressure is applied by natural expansion of the heart during diastole. The therapeutic agent is thus applied to the tissue in a gentle manner that avoids disrupting or injuring healthy cardiac or other tissue, while diffusion of the therapeutic agent into the tissue is facilitated by the application of the pressure exerted during diastole. At the same time, pressure between the heart and the jacket effectively forms a seal that prevents the therapeutic agent from diffusing to areas in the body other than the treatment area. The hydrogel polymer can be biodegradable or non-degradable, as described above for the polymeric matrix material.

Alternatively, the delivery source comprises a chemical/polymer bioadhesive system used to adhere the device of the invention to the heart. The polymer system used for adhesion of the jacket to the heart is modified to include one or more therapeutic agent(s). The amount of therapeutic agent included in the bioadhesive system is influenced by such factors as listed above, including desired dosage of the agent, solubility of the agent, and the molecular weight of the agent versus the molecular weight of the polymer. Moreover, how the agent loading affects the physical and/or chemical characteristics of the polymer bioadhesive will be considered.

In another embodiment of the present invention, the delivery source is provided as an element that is separate from the jacket of the device. The delivery source can be provided in the form of a patch containing the therapeutic agent of interest, or a bladder containing the therapeutic agent. Suitable patches and bladders are known in the art. For example, see *Epicardial Administration of Ibutilide from Polyurethane matrixes: Effects on Defibrillation Threshold and Electrophysiologic Parameters*, Labhasetwar et al., J. Of Cardiovascular Pharm., 24:826–840 (1994), *Sotalol Controlled-Release Systems for Arrhythmias: In Vitro Characterization, In Vivo Drug Disposition, and Electrophysiologic Effects*, Labhasetwar et al., J. of Pharm. Sciences, 83: 156–164 (1994).

When the delivery source comprises a bladder, the bladder is preferably refillable. Refilling the bladder can be achieved in any suitable manner, e.g., using a catheter connected to the bladder containing a proximal terminal connection just under the surface of the skin, or through a one-use direct injection of therapeutic agent from a disposable hypodermic needle.

In this embodiment, the jacket provides an anchoring surface for the delivery source that presses the delivery source against the surface of the heart and maintains the delivery source in position on the heart. According to the invention, the patch or bladder can be provided underneath the jacket 10, such that the delivery source is positioned between the jacket and the heart. The jacket presses the delivery source against the heart, without causing damage to the heart that would result from directly attaching the source at the treatment site, by sutures, adhesives or the like. The delivery source can be attached to the jacket, for example, using sutures or bioadhesives, to maintain the position of the delivery source in relation to the jacket. Alternatively, the patch or bladder can be held in place simply by the pressure of the jacket against the heart. Because the jacket itself is maintained in non-shifting contact with the heart, the delivery source is also provided with a non-shifting position on the surface of the heart. For example, the use of the jacket to maintain the positioning of the delivery source avoids such undesirable effects as fibrosis, necrosis, and the like.

The patch or bladder is fabricated from a biocompatible material, to avoid adverse effects associated with rejection, infection, and the like. The amount of therapeutic agent provided in such patches or bladders depends upon such factors as those listed above for the delivery source as a coating.

Delivery of the therapeutic agent to target tissues can be achieved through passive as well as active delivery methods. Passive methods include diffusion of the agent from the delivery source, as discussed above. Active delivery mechanisms use an energy source to deliver the therapeutic agent to the target tissue.

Active delivery systems include systems that use an energy source to deliver one or more therapeutic agents to the target tissue. Suitable energy sources include external sources such pumps or sources of electrical current. For example, an osmotic pump can be used in connection with a bladder delivery source, to provide active delivery of agents from the bladder to target tissues. Examples of sources of electrical current include batteries and electrodes. For example, the device of the invention can utilize iontophoresis to deliver one or more therapeutic agents to the heart. Iontophoresis uses electrical current, through a direct myocardial electrode patch, to transport charged molecules into tissue. Iontophoretic methods are known in the art, as are methods using phonophoresis and battery-driven devices. Other suitable external energy sources include ultrasound, thermal energy, radiofrequency, or microwave energy.

In yet another embodiment, the natural movement of the heart is used as an energy source for therapeutic agent delivery. As described above, when the delivery source of the invention comprises a hydrogel, diastolic filling of the heart can drive release of the therapeutic agent from the hydrogel coating. In this embodiment, the hydrogel can be selected to allow release of a desired dosage of the therapeutic agent from the hydrogel polymer coating during compression of the hydrogel polymer coating against the heart or other tissue. The pumping action of the heart induces the device to release the agent, and the therapeutic agent is effectively released upon compression of the polymer coating on the device. When the heart expands during diastole, it exerts pressure against the jacket of the device, which in turn compresses the coating against the heart. Compression of the coating triggers release of the agent for transfer into or onto the target tissue. The pressure applied to the fluid therapeutic agent against the tissue by the jacket enhances transfer of the therapeutic agent into the tissue. The pressure is sufficient to allow release of the therapeutic agent without damaging the tissue. Similarly, movement of the heart can be used to drive release of the therapeutic agent from a bladder or patch.

In another embodiment, one or more therapeutic agents are delivered to the surface of the heart by injecting the agents into the myocardium through microneedles provided on the surface of the delivery source. Preferably, the delivery source comprises a bladder, and fine microneedles are connected to the bladder to provide a channel through which the therapeutic agents are transported into myocardium. In one embodiment, pneumatic pressure for infusing the therapeutic agent is provided by pressurizing the bladder with a catheter containing a proximal terminal connection routed to a location just under the patient's skin for easy access. Alternatively, energy transduced from diastolic filling of the heart can provide pressure for infusing the therapeutic agent. Diastolic filling of the heart applies pressure to the bladder, as the expanding heart encounters the restraining force of the jacket. This in turn causes release of the agent to target tissues.

As contemplated by the present invention, a therapeutic agent can be delivered to the heart or surrounding tissue of interest for a period of from several minutes, to several weeks.

The present invention provides improved capacity to deliver one or more therapeutic agents to one or more selected sites on the heart surface. The jacket of the invention encompasses all or a part of the heart, and all, or one or more selected areas of the jacket can be provided with a delivery source according to the invention.

In a particular aspect, the invention provides a delivery source that can be either bi-directional or uni-directional. Bi-directional release of the therapeutic agent is desirable, for example, when preventing adhesion between the heart and surrounding tissues. For example, when the target tissue is the heart, the delivery source can be adapted to release the therapeutic agent towards the heart only. In one embodiment, this uni-directional release can be accomplished by providing a coating containing the therapeutic agent on the jacket facing the heart only. Alternatively, when the target tissue is the tissue surrounding the heart, the delivery device can be adapted to release the therapeutic agent away from the heart, and thus towards the target tissues.

In one embodiment, the jacket material of the device can be fashioned in such a way that therapeutic agents retained in the delivery source are released only in the direction of the heart by modifying the porosity of the jacket material. In this embodiment, the portion of the jacket facing or adjacent the heart has porosity large enough to allow the therapeutic agent to diffuse from the jacket and into the myocardium. The portion of the jacket facing away from the heart can be modified to be non-porous, or to contain pores of insufficient size to allow therapeutic agents to pass through. Alternatively, if the target tissue comprises tissue surrounding the heart, the jacket material can be modified such that therapeutic agent delivery is directed away from the heart, and towards the surrounding tissues. In yet another embodiment, an impermeable layer can be provided to create a barrier to prevent delivery of the therapeutic agent to a particular area of tissue. Delivery of the agent will, in this embodiment, occur in a direction opposite the barrier.

When the delivery source is provided in the form of a separate bladder or patch, the permeability of the delivery source can be adapted to allow selective release of the agent to target tissues, using the modification of porosity described above for the coating. Alternatively, an impermeable layer, as discussed above, can be provided in connection with the bladder or patch, to achieve directed delivery of the agent.

In one embodiment, the present invention provides for delivery to selected target areas of the heart and/or surrounding tissue. In this embodiment, delivery of the therapeutic agent is precisely controlled, so that only selected areas are exposed to the agent. This can be achieved, for example, by coating only a desired area of the jacket 10 with the therapeutic agent, when the delivery source is provided in the form of a coating on the jacket. Alternatively, when the delivery source comprises a separate bladder or patch, the location of the delivery source can be controlled to expose only a limited target area to the agent or agents. For example, it may be desirable to apply an anti-fibrotic agent over areas of the heart including arteries, so that if it is necessary to access the arteries for future coronary artery repair, there would be no adhesion between the jacket and the heart.

Unlike solid drug delivery devices known in the art, the present invention provides a jacket of a knit biocompatible material that provides sustained, controlled release of a therapeutic agent to the heart or other target tissue. When the delivery source comprises a coating on the jacket, the jacket material provides a larger surface area for application of therapeutic agent(s), as well as a flexible device to maintain intimate, non-shifting contact with the target tissue. The structure of the knit material allows the device to carry larger dosages of one or more therapeutic agents. Moreover, the jacket of the invention can be adapted to encompass the lower portion of the heart, the upper portion of the heart, or substantially the entire surface of the heart. Regardless of the surface area of the heart encompassed by the jacket of the invention, the delivery source of the device can be located at any desired target area, e.g., a specific surface artery of the heart or area of ischemia or necrosis.

It is understood that although the invention has been described in connection with heart applications, the methods and device described herein can be readily adapted for a variety of tissues in the body, using the teachings herein.

While a preferred embodiment of the present invention has been described, it should be understood that various changes, adaptations and modifications may be made therein without departing from the spirit of the invention and the scope of the appended claims.

What is claimed is:

1. A device for treating cardiac disease of a heart having an upper portion and a lower portion divided by an A-V groove, the device comprising:
   a. a jacket of flexible material defining a volume between an upper end and a lower end, the jacket adapted to be secured to the heart and adapted to be adjusted on the heart to snugly conform to an external geometry of the heart to constrain expansion of the heart during diastole and permit substantially unimpeded contraction of the heart during systole; and
   b. a non-adherent lining in association with the jacket wherein the non-adherent lining is provided in the form of one or more ribs extending from a base to an apex of the heart.

2. A device for treating cardiac disease of a heart having an upper portion and a lower portion divided by an A-V groove, the device comprising:
   a. a jacket of flexible material defining a volume between an upper end and a lower end, the jacket adapted to be secured to the heart and adapted to be adjusted on the heart to snugly conform to an external geometry of the heart to constrain expansion of the heart during diastole and permit substantially unimpeded contraction of the heart during systole;
   b. a non-adherent lining in association with the jacket; and
   c. a delivery source for the delivery of one or more therapeutic agents to the surface of the heart.

3. The device according to claim 2 wherein the device provides localized delivery of the one or more therapeutic agents to a target area on the surface of the heart.

4. The device according to claim 2 wherein the therapeutic agent comprises a pharmacological agent.

5. The device according to claim 2 wherein the therapeutic agent comprises cellular material.

6. The device according to claim 2 wherein the delivery source comprises a coating on the jacket.

7. The device according to claim 2 wherein the delivery source comprises a separable element from the jacket.

8. The device according to claim 2 wherein the delivery source for the delivery of one or more therapeutic agents is provided at an area of the jacket that overlaps an area of the non-adherent material.

9. The device according to claim 8 wherein the non-adherent material is permeable to the therapeutic agent(s).

10. The device according to claim 2 wherein the delivery source for the delivery of one or more therapeutic agents is provided at an area of the jacket that is separate from an area of the non-adherent material.

11. A method for treating cardiac disease, the method comprising:
   a. surgically accessing the heart;
   b. applying a treatment device on the heart, the device comprising:
      1) a jacket of flexible material defining a volume between an upper end and a lower end, the jacket adapted to be secured to the heart and adapted to be adjusted on the heart to snugly conform to an external geometry of the heart to constrain circumferential expansion of the heart during diastole and permit substantially unimpeded contraction of the heart during systole; and
      2) a non-adherent lining in association with the jacket, wherein the non-adherent lining is provided in the form of one or more ribs extending from a base to an apex of the heart;
   c. securing the treatment device to the heart; and
   d. surgically closing access to the heart while leaving the treatment device on the heart.

12. A method for treating cardiac disease, the method comprising:
   a. surgically accessing the heart;
   b. applying a treatment device on the heart, the device comprising:
      1) a jacket of flexible material defining a volume between at upper end and a lower end, the jacket adapted to be secured to the heart and adapted to be adjusted on the heart to snugly conform to an external geometry of the heart to constrain circumferential expansion of the heart during diastole and permit substantially unimpeded contraction of the heart during systole;
      2) a non-adherent lining; and
      3) a delivery source for delivery of one or more therapeutic agents to the surface of the heart;
   c. securing the treatment device to the heart; and
   d. surgically closing access to the heart while leaving the treatment device on the heart.

13. The method according to claim 12, wherein the one or more therapeutic agents comprise one or more pharmacological agents.

14. The method according to claim 12 wherein the one or more therapeutic agents comprise cellular material.

15. A device for treating cardiac disease of a heart having an upper portion and a lower portion divided by an A-V groove, the device comprising:
   a. a jacket of flexible material defining a volume between an upper end and a lower end, the jacket adapted to be secured to the heart and adapted to be adjusted on the heart to snugly conform to an external geometry of the heart to constrain expansion of the heart during diastole and permit substantially unimpeded contraction of the heart during systole; and b. a non-adherent coating in association with the jacket, wherein the non-adherent coating is configured to cover only selected areas of the heart.

16. The device according to claim 15 wherein the jacket comprises an elastic material.

17. The device according to claim 15, wherein the jacket comprises an open cell material.

18. A device for treating cardiac disease of a heart having an upper portion and a lower portion divided by an A-V groove, the device comprising:

a. a jacket comprised of an open cell flexible material defining a volume between an upper end and a lower end, the jacket adapted to be secured to the heart and adapted to be adjusted on the heart to snugly conform to an external geometry of the heart to constrain expansion of the heart during diastole and permit substantially unimpeded contraction of the heart during systole; and b. a non-adherent coating in association with the jacket wherein the open cell material defines interstitial spaces and the non-adherent coating fills the interstitial spaces defined by the open cell material.

19. A device for treating cardiac disease of a heart having an upper portion and a lower portion divided by an A-V groove, the device comprising:

a. a jacket of flexible material defining a volume between an upper end and a lower end, the jacket adapted to be secured to the heart and adapted to be adjusted on the heart to snugly conform to an external geometry of the heart to constrain expansion of the heart during diastole and permit substantially unimpeded contraction of the heart during systole, the jacket comprising a biodegradable material; and b. a non-adherent coating in association with the jacket.

20. A device for treating cardiac disease of a heart having an upper portion and a lower portion divided by an A-V groove, the device comprising:

a. a jacket of flexible material defining a volume between an upper end and a lower end, the jacket adapted to be secured to the heart and adapted to be adjusted on the heart to snugly conform to an external geometry of the heart to constrain expansion of the heart during diastole and permit substantially unimpeded contraction of the heart during systole; and b. a non-adherent coating in association with the jacket, wherein the non-adherent material provided in the form of one or more ribs extending from a base to an apex of the heart.

21. A device for treating cardiac disease of a heart having an upper portion and a lower portion divided by an A-V groove, the device comprising:

a. a jacket of flexible material defining a volume between an upper end and a lower end, the jacket adapted to be secured to the heart and adapted to be adjusted on the heart to snugly conform to an external geometry of the heart to constrain expansion of the heart during diastole and permit substantially unimpeded contraction of the heart during systole;

b. a non-adherent coating in association with the jacket; and c. a delivery source for the delivery of one or more therapeutic agents to the surface of the heart.

22. The device according to claim 21 wherein the device provides localized delivery of the one or more therapeutic agents to a target area on the surface of the heart.

23. The device according to claim 21 wherein the therapeutic agent comprises a pharmacological agent.

24. The device according to claim 21 wherein the therapeutic agent comprises cellular material.

25. The device according to claim 21 the delivery source comprises a coating on the jacket.

26. The device according to claim 21 wherein the delivery source comprises a separable element from the jacket.

27. The device according to claim 21 wherein the delivery source for the delivery of one or more therapeutic agents is provided at an area of the jacket that overlaps an area of the non-adherent material.

28. The device according to claim 21 wherein the non-adherent material is permeable to the therapeutic agent(s).

29. The device according to claim 21 wherein the delivery source for the delivery of one or more therapeutic agents is provided at an area of the jacket that is separate from an area of the non-adherent material.

30. A method for treating cardiac disease, the method comprising:

a. surgically accessing the heart;

b. applying a treatment device on the heart, the device comprising:

1) a jacket of flexible material defining a volume between an upper end and a lower end, the jacket adapted to be secured to the heart and adapted to be adjusted on the heart to snugly conform to an external geometry of the heart to constrain circumferential expansion of the heart during diastole and permit substantially unimpeded contraction of the heart during systole; and 2) a non-adherent coating in association with the jacket, wherein the non-adherent coating is configured to contact only selected areas of the heart;

c. securing the treatment device to the heart; and d. surgically closing access to the heart while leaving the treatment device on the heart.

31. A method for treating cardiac disease, the method comprising:

a surgically accessing the heart;

b. applying a treatment device oil the heart, the device comprising:

1) a jacket of flexible material defining a volume between an upper end and a lower end, the jacket adapted to be secured to the heart and adapted to be adjusted on the heart to snugly conform to an external geometry of the heart to constrain circumferential expansion of the heart during diastole and permit substantially unimpeded contraction of the heart during systole; and 2), a non-adherent coating in association with the jacket, wherein the non-adherent material is provided in the form of one or more ribs extending from a base to an apex of the heart;

c. securing the treatment device to the heart; and d. surgically closing access to the heart while leaving the treatment device on the heart.

32. A method for treating cardiac disease, the method comprising:
- a. surgically accessing the heart;
- b. applying a treatment device on the heart, the device comprising:
    1) a jacket of flexible material defining a volume between an upper end and a lower end, the jacket adapted to be secured to the heart and adapted to be adjusted on the heart to snugly conform to an external geometry of the heart to constrain circumferential expansion of the heart during diastole and permit substantially unimpeded contraction of the heart during systole;
    2) a non-adherent coating in association with the jacket; and
    3) a delivery source for delivery of one or more therapeutic agents to the surface of the heart;
- c. securing the treatment device to the heart; and
- d. surgically closing access to the heart while leaving the treatment device on the heart.

33. The method according to claim 31, wherein the one or more therapeutic agents comprise one or more pharmacological agents.

34. The method according to claim 31 wherein the one or more therapeutic agents comprise cellular material.

35. The device according to claim 31, wherein the jacket comprises an open cell material.

36. The device according to claim 35, wherein the open cell material defines interstitial spaces and the non-adherent coating fills the interstitial spaces defined by the open cell material.

* * * * *

UNITED STATES PATENT AND TRADEMARK OFFICE
CERTIFICATE OF CORRECTION

PATENT NO. : 6,730,016 B1
DATED : May 4, 2004
INVENTOR(S) : Cox et al.

It is certified that error appears in the above-identified patent and that said Letters Patent is hereby corrected as shown below:

Title page,
Item [56], References Cited, U.S. PATENT DOCUMENTS, please insert the following
-- 3,983,863  10/1976  Janke et al. --

Column 30,
Line 9, "to claim 21 the" should read -- to claim 21 wherein the --
Line 17, "according to claim 21" should read -- according to claim 27 --
Line 48, "a surgically accessing" should read -- a. surgically accessing --
Line 60, "2), a non-adherent" should read -- 2) a non-adherent --

Signed and Sealed this

Twenty-seventh Day of July, 2004

JON W. DUDAS
*Acting Director of the United States Patent and Trademark Office*